(12) United States Patent
Brandt et al.

(10) Patent No.: US 10,111,482 B2
(45) Date of Patent: Oct. 30, 2018

(54) COOLING ASSEMBLY

(71) Applicant: NIKE, Inc., Beaverton, OR (US)

(72) Inventors: Baron C. Brandt, Portland, OR (US);
Daniel A. Judelson, Portland, OR (US);
Rebecca P. Hurd, Tigard, OR (US);
Phyllis Michele Liniger, St. Helens, OR (US); Tyler C. Lynch, Portland, OR (US); Nina Nguyen, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 214 days.

(21) Appl. No.: 14/966,449

(22) Filed: Dec. 11, 2015

(65) Prior Publication Data
US 2016/0165992 A1  Jun. 16, 2016

Related U.S. Application Data

(60) Provisional application No. 62/091,315, filed on Dec. 12, 2014, provisional application No. 62/154,434, filed on Apr. 29, 2015.

(51) Int. Cl.
A42B 1/00 (2006.01)
A42C 5/04 (2006.01)
(Continued)

(52) U.S. Cl.
CPC .............. *A42B 1/008* (2013.01); *A42B 1/046* (2013.01); *A42B 1/066* (2013.01); *A42C 5/04* (2013.01); *A61F 7/02* (2013.01); *A61F 7/10* (2013.01); *A61F 2007/0003* (2013.01); *A61F 2007/0004* (2013.01); *A61F 2007/0008* (2013.01); *A61F 2007/026* (2013.01); *A61F 2007/0215* (2013.01); *A61F 2007/0222* (2013.01); *A61F 2007/0228* (2013.01); *A61F 2007/0231* (2013.01); *A61F 2007/108* (2013.01)

(58) Field of Classification Search
CPC ........... A42C 5/04; A42B 1/008; A42B 1/046; A42B 1/066; A61F 7/02; A61F 7/10; A61F 2007/0003; A61F 2007/0004; A61F 2007/0008

See application file for complete search history.

(56) References Cited

U.S. PATENT DOCUMENTS 5,016,287 A * 5/1991 Harris .................... A42B 1/045
                                                    2/202
5,630,230 A * 5/1997 Fujino .................. A41D 20/005
                                                   2/200.1

(Continued)

FOREIGN PATENT DOCUMENTS

WO      9921517 A1    5/1999

OTHER PUBLICATIONS

International Search Report with Written Opinion dated Mar. 21, 2016 in PCT Application No. PCT/US2015/065512, 15 pages.

(Continued)

*Primary Examiner* — Shaun R Hurley
*Assistant Examiner* — Andrew W Sutton
(74) *Attorney, Agent, or Firm* — Shook, Hardy & Bacon L.L.P.

(57) ABSTRACT

A cooling headgear is disclosed. Absorbent material within the headgear retains cold water. When worn by a user, the headgear holds the cold water to the head of the user, cooling the user.

19 Claims, 25 Drawing Sheets

(51) Int. Cl.
*A42B 1/04* (2006.01)
*A42B 1/06* (2006.01)
*A61F 7/02* (2006.01)
*A61F 7/10* (2006.01)
*A61F 7/00* (2006.01)

(56) References Cited

U.S. PATENT DOCUMENTS

| | | | |
|---|---|---|---|
| 5,887,276 A | 3/1999 | Lee | |
| 6,319,599 B1* | 11/2001 | Buckley | A61F 7/02 2/2.15 |
| 2003/0208831 A1 | 11/2003 | Lazar et al. | |
| 2003/0233697 A1 | 12/2003 | Tsai | |
| 2005/0097658 A1* | 5/2005 | Lyons | A41F 15/007 2/267 |
| 2011/0016610 A1 | 1/2011 | Wieder | |
| 2014/0352033 A1* | 12/2014 | Bryan | A42B 3/04 2/244 |

OTHER PUBLICATIONS

International Preliminary Report on Patentability dated Jun. 22, 2017 in International Patent Application No. PCT/US2015/065512, 10 pages.

* cited by examiner

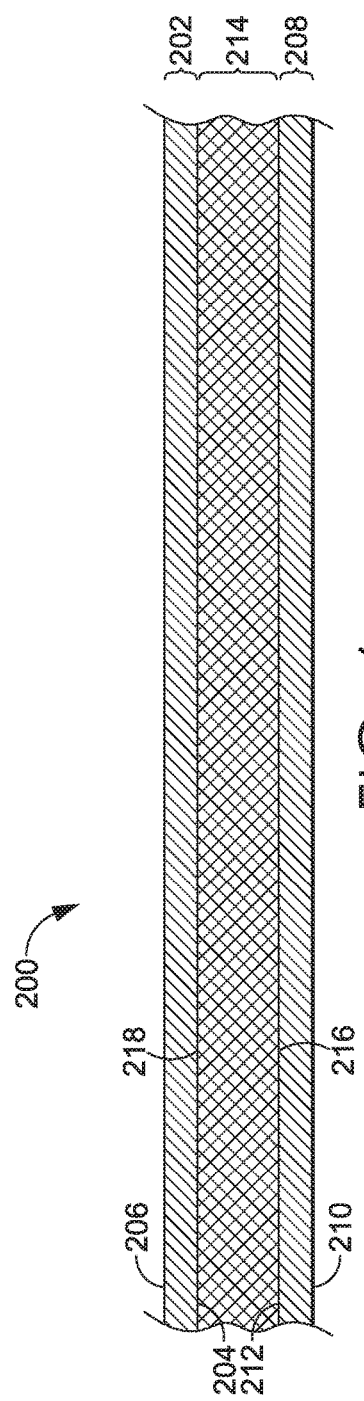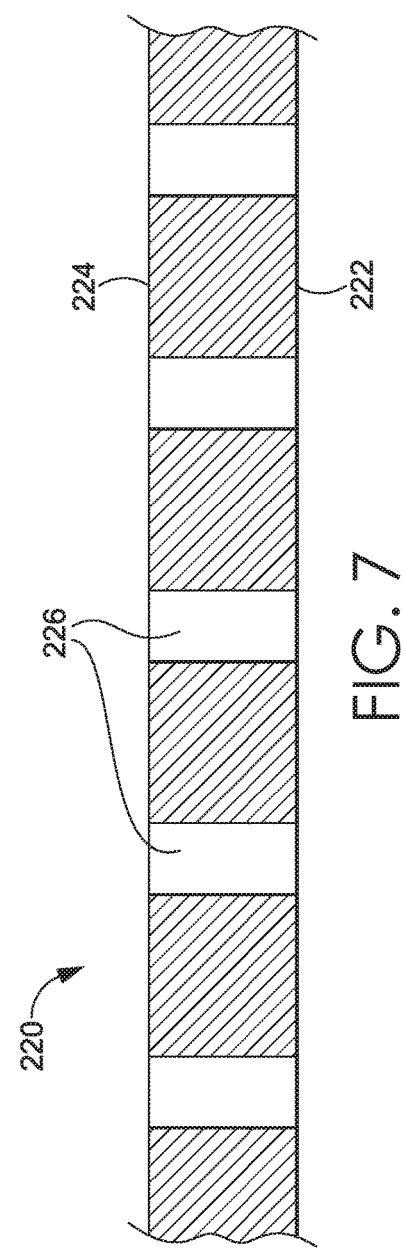

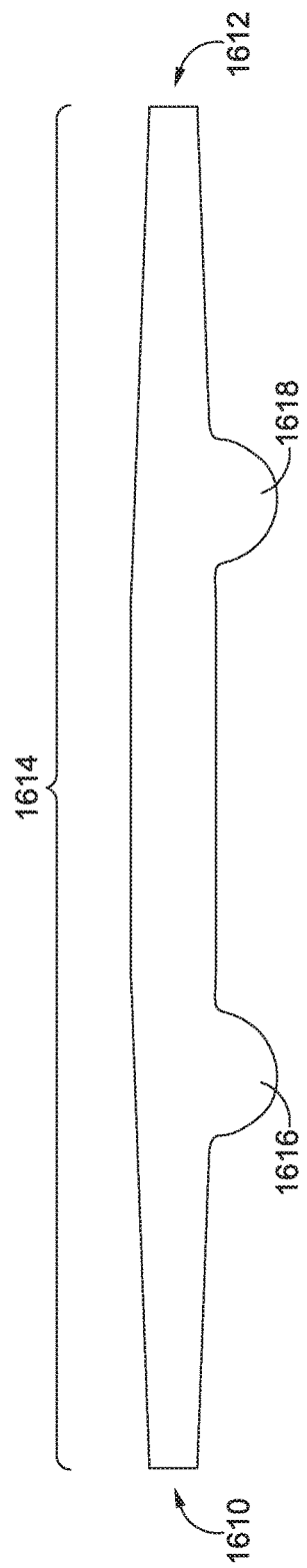

COOLING ASSEMBLY

CROSS-REFERENCE TO RELATED APPLICATIONS

This application entitled "Cooling Assembly" claims the benefit of priority of U.S. Provisional Application No. 62/091,315, entitled "Cooling Headgear," filed Dec. 12, 2014, and U.S. Provisional Application No. 62/154,434, entitled "Cooling Headgear," filed Apr. 29, 2015. The entirety of the aforementioned applications is incorporated herein.

STATEMENT REGARDING FEDERALLY SPONSORED RESEARCH OR DEVELOPMENT

Not applicable.

BACKGROUND

A great many outdoor recreational activities are best enjoyed during the warmer months of the year. However, there are drawbacks to engaging in physical activity in conditions that are too hot. One of the risks of exercising outdoors in high temperatures is overheating. This is problematic as overheating may lead to dehydration, cramping, heat exhaustion, and even heat stroke.

One method for counteracting rising body temperatures during exercise is to apply cold water to parts of the body where blood vessels are close to the surface of the skin. As blood circulates, the cold water dissipates heat from the body. The head in particular experiences a significant increase in flow of blood during exercise. For this reason, a common remedy to overheating due to physical exertion is applying a cold, wet towel or cloth to the head. However, this method typically requires the person to stop their activity to hold the towel to his or her head. It may be possible to wrap the towel or cloth around the head or neck of the person, but the towel or cloth will shift as the person moves. An additional drawback to this method is that the water typically drips from the towel and could run into the person's eyes, causing visibility problems during activity.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

At a high level, aspects described herein relate to a cooling headgear, mask, and headband (collectively or individually known as a cooling assembly) constructed of an absorbent material. The absorbent material may be held between two layers of elastomeric material such that the absorbent material is held securely to a user's head. When saturated with cold water, the absorbent material of the assembly retains the liquid, and the elastomeric material helps to prevent leakage. The elastomeric properties of the cooling assembly allow for it to be taken on and off easily and prevent the cooling assembly from shifting on the user's head during activity. The cooling assembly is also portable and reusable. This and other aspects will be discussed in further detail in the Detailed Description.

BRIEF DESCRIPTION OF THE DRAWINGS

The present invention is described in detail herein with reference to the attached drawing figures, wherein:

FIG. 6 depicts a cross-section view of an exemplary cooling headgear material in accordance with aspects herein;

FIG. 7 depicts a cross-section view of an exemplary cooling headgear material in accordance with aspects herein;

FIG. 16B depicts a plan view of the exemplary cooling headband of FIG. 16A in a laid-flat arrangement in accordance with aspects herein.

DETAILED DESCRIPTION

Provided herein is a cooling assembly such as a headgear, an eye mask, and/or a cooling headband which, when worn by a user, cools down the body of the user. The cooling assembly is designed to retain or hold liquid such that when a cold liquid, such as water, is applied to the cooling assembly and the assembly is worn by the user, evaporation of the water helps cool the body of the user. Moreover, when wearing the cooling assembly, the user experiences a sense of cooling due to the cool liquid being in contact with the user's head.

In exemplary aspect, the cooling assembly is formed in whole or in part of an absorbent material held between two layers of elastomeric material. The absorbent material retains or holds cold water and the elastomeric material holds the cooling assembly securely onto the head of the user. The elastomeric material may be designed to retain the water in the absorbent material, preventing water from dripping into the eyes of the user when the cooling assembly is worn. This enables the user to cool his or head without using his or her hands, thus freeing the user to do other activities while wearing the cooling assembly.

In exemplary aspects, when the cooling assembly is in the form of a headgear it may comprise optional features such as a neck flap and/or a neck and shoulder flap that can also be saturated with liquid. When worn by the user, the flap rests against the neck and/or shoulders of the user and further helps to cool the user. In aspects, the neck flap may be permanently affixed to the cooling headgear and in other aspects, the neck flap may be removably affixed to the headgear. In an additional alternative aspect, a cooling eye mask may be used alone or in combination with the cooling headgear. The eye mask may be saturated with a liquid and placed over the eye area of the user further heightening the cooling effects of the headgear system. In yet another alternative aspect, the cooling assembly may be in the form of a headband that can be worn across the forehead area of the user to help cool the user.

Figure 1:
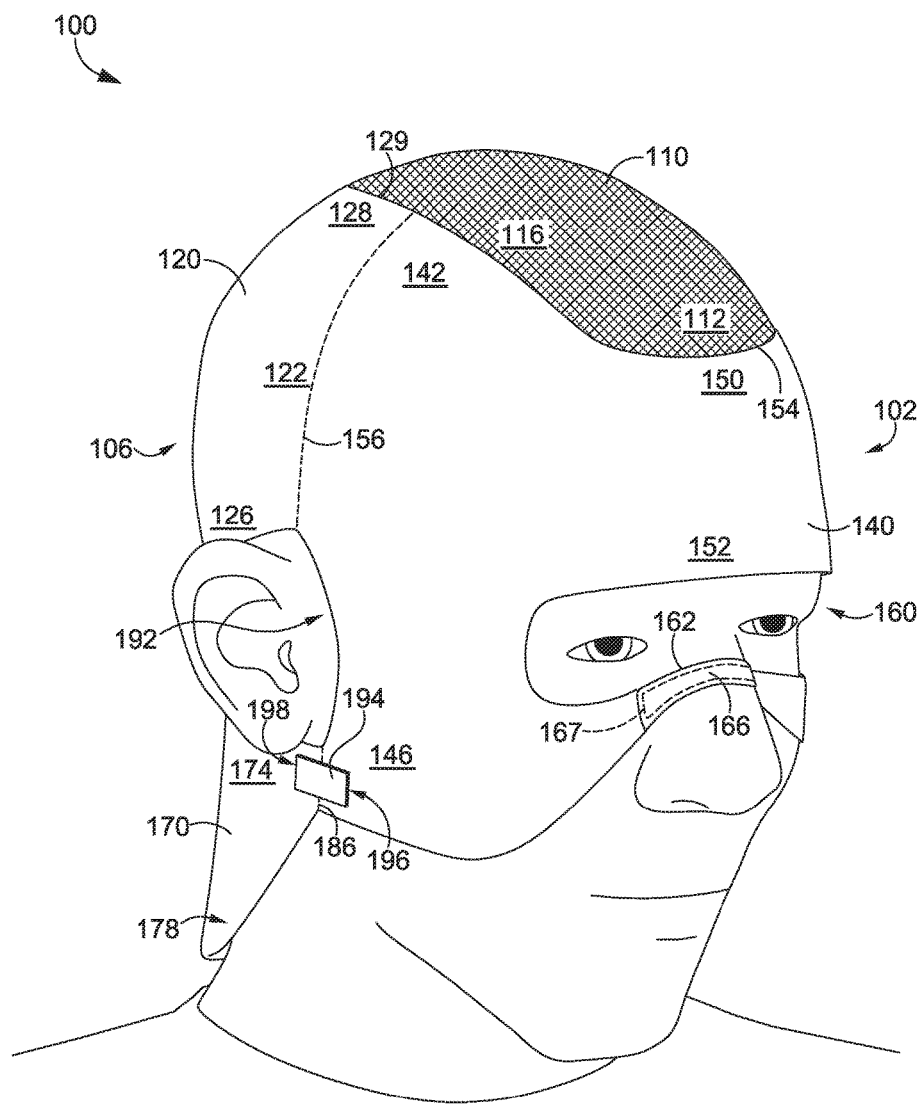
FIG. 1 depicts a front perspective view of an exemplary cooling headgear as worn by a user in accordance with aspects herein.

Referring now to FIG. 1, a front perspective view of an exemplary cooling headgear 100 is illustrated in accordance with aspects herein. The cooling headgear 100 may be worn over the head of a user, as shown. FIG. 1 depicts an anterior aspect 102 and right portion aspect 106 of the cooling headgear 100. In exemplary aspects, in this view the cooling headgear 100 may comprise a face panel 140, a vent panel 110, a right panel 120, and a neck panel 170. An anterior portion 122, inferior side 126, and superior side 128 of the right panel 120 are visible. Also shown are a right superior portion 142, right inferior portion 146, center superior portion 150, and center inferior portion 152 of the face panel 140. An anterior portion 112 and right side 115 of the vent panel 110 are shown at the top of the headgear 100, and a right superior portion 174 of a neck panel 170 is shown at the bottom of the headgear 100.

The right panel 120, face panel 140, and neck panel 170 may be comprised of a mask material. As shown in a sectional view in FIG. 6, the mask material 200 may have an exterior material layer 202, an interior material layer 208, and an absorbent material layer 214 disposed between the exterior material layer 202 and the interior material layer 208. The exterior material layer 202 has an inner-facing surface 204 and an outer-facing surface 206. Similarly, the interior material layer 208 has an inner-facing surface 212 and an outer-facing surface 210. The absorbent material layer 214 comprises a first surface 216 and a second surface 218. As shown in FIG. 6, the absorbent material layer 214 is maintained between the exterior material layer 202 and the interior material layer 208 such that the second surface 218 of the absorbent material layer 214 contacts the inner-facing surface 204 of the exterior material layer 202. And the first surface 216 of the absorbent material layer 214 contacts the inner-facing surface 212 of the interior material layer 208. When the cooling headgear 100 is worn by a user, the outer-facing surface 210 of the interior material layer 208 contacts the user's head and the outer-facing surface 206 of the exterior material layer 202 faces away from the user.

In an exemplary aspect, both the interior material layer 208 and the exterior material layer 202 are comprised of an elastomeric material. The elastomeric material may be, for example, comprised of fabric made of polyester and spandex. Such fabric may be stretch woven in order to retain the absorbent material and water within the headgear. Moreover, the fabric may exhibit four-way stretch so as to closely conform to a user's head when the headgear 100 is worn. Alternatively, the interior material layer 208 and exterior material layer 202 may be made of different materials such as a knit material. For example, the interior material layer 208 may be made of a material designed to feel comfortable against a user's skin or a material designed to wick moisture away from the skin.

In exemplary aspects, the absorbent material layer 214 is comprised of a hydrophilic material. Preferably, the hydrophilic material is comprised of a superabsorbent woven or non-woven fiber. Such fibers may be quilted into a sheet to provide structure to the material. Preferably, the superabsorbent fiber is comprised of a cross-linked terpolymer. Such terpolymer may be produced by polymerizing acrylic acid, methyl acrylate, and sodium hydroxide in water. In an exemplary implementation of the current invention, the absorbent material layer 214 is comprised of Super Absorbent Fibre (SAF®) produced by Technical Absorbents Limited and is quilted into flat panels. Alternatively, the absorbent material layer 214 may be comprised of other hydrophilic materials such as natural fibers, synthetic fibers, or gel polymers. In one exemplary aspect, the absorbent material layer 214 may be formed of a super absorbent microfiber that is highly absorbent but yet is able to release moisture vapor, thereby allowing the absorbent material layer 214 to dry faster. The super absorbent microfiber could be used in conjunction with the superabsorbent fiber discussed above or in place of the superabsorbent fiber. Exemplary superabsorbent microfibers may comprise Delta-Peak™ or NanoFront® fibers produced by Teijin Limited located in Osaka, Japan.

The layers of the mask material 200 may be held together by bonding, adhesive, taping, stitching, quilting, or otherwise affixing the layers 202, 208, and 214 together. In one exemplary aspect, the absorbent material layer 214 may be held between the exterior material layer 202 and the interior material layer 208 by bonding the exterior material layer 202 directly to the interior material layer 208 at the perimeter edges of the headgear 100. Alternatively, the inner-facing surface 204 of the exterior material layer 202 may be bonded to the second surface 218 of the absorbent material layer 214 and the inner-facing surface 212 of the interior material layer 208 may be bonded to the first surface 216 of the absorbent material layer 214.

In one exemplary aspect, the layers of the mask material 200 may be bonded together with an adhesive. The adhesive may be a pressure-sensitive adhesive, a contact adhesive, a hot melt adhesive, or a synthetic adhesive. In one exemplary aspect, the layers of the mask material 200 are held together with an adhesive film. Such adhesive film may be elastomeric to allow the bonded material to flex. Preferably, the adhesive is comprised of ester polyurethane. An exemplary adhesive is Sewfree® 3415 produced by Bemis.

Referring back to FIG. 1, the superior side 128 of the right panel 120 is attached to the right side 116 of the vent panel 110 at seam 129. The center superior portion 150 of the face panel 140 is attached to the anterior portion 112 of the vent panel 110 at seam 154. The right superior portion 142 of the face panel 140 is attached to the anterior portion 122 of the right panel 120 at seam 156. Attachments between the panels of the cooling headgear 100 at the various seams may be accomplished by a number of affixing technologies including stitching, bonding, hook-and-loop fasteners, and the like. In an exemplary aspect, the panels are joined by bonding the seams together with an adhesive film. An exemplary adhesive film is Sewfree® 3415 produced by Bemis.

The cooling headgear 100 may optionally comprise an eye opening 160, as shown in FIG. 1 and FIG. 4. The eye opening 160 is located proximate to the center inferior portion 152 of the face panel 140 and extends through the exterior material layer 202, interior material layer 208, and absorbent material layer 214 of the mask material 200. Preferably, the eye opening 160 is positioned such that a user may see through the eye opening 160 when wearing the headgear 100.

In examples wherein the cooling headgear 100 comprises the eye opening 160, the cooling headgear 100 may also comprise a nose bridge 166 located inferior to the eye opening 160. The nose bridge 166 defines an inferior edge 162 of the eye opening 160. In an exemplary aspect, the nose bridge 166 comprises a rigid material 167 which aids in securing the nose bridge 166 to the nose of the user. Exemplary materials may comprise plastic, metal, rubber, silicone, polyurethane, stiff fabrics, and the like. The rigid material 167 may be placed and affixed, for example, between the exterior material layer 202 and the absorbent material layer 214 of the mask material 200, or between the interior material layer 208 and the absorbent material layer 214. The rigid material 167 may also be attached to the outer-facing surface 206 of the exterior material layer 202 or the outer-facing surface 210 of the interior material layer 208. The rigid material 167 may be secured by stitching, bonding, or similar attachment technologies.

As illustrated in FIG. 1, the right inferior portion 146 of the face panel 140 may be attached to the right superior portion 174 of the neck panel 170 at a seam 186 to form an optional right ear opening 192. The ear opening 192 may be generally circular in shape and is configured to allow a user's ear to remain uncovered by the headgear 100. The seam 186 may be formed by any of the affixing technologies listed above. Alternatively, the seam 186 may be secured using a fastener 194, as shown. A first end 196 of the fastener 194 may be affixed to the right inferior portion 146 of the face panel 140 and a second end 198 of the fastener 194 may be affixed to the right superior portion 174 of the neck panel 170. The fastener 194 may be any of a number of reversible attachment mechanisms including, for example, hook-and-loop fasteners, buttons, snaps, buckles, clips, clasps, a magnetic plate, or hook-and-eye fasteners, and the like.

Alternatively, the ear opening 192 may be covered with a porous material, as shown in FIG. 7. With respect to FIG. 7, the porous material 220 comprises an inner surface 222 and an outer surface 224 through which apertures or pores 226 extend. Air may pass through the pores 226 in the porous material 220. In exemplary aspects, the porous material 220 may also be used to form the vent panel 110, thus enabling sweat and water to evaporate from the user's head through the vent panel 110. Additionally, the pores 226 may allow ambient air to reach the user's head when the headgear 100 is worn. The porous material 220 may be comprised of, for example, a woven or knit fabric comprised of cotton, linen, nylon, polyester, rayon, or silk. In one aspect, the porous material 220 may be a mesh fabric comprised of polyester and spandex. Alternatively, the porous material 220 may be comprised of the same elastomeric material as is used for the interior material layer 208 and exterior material layer 202 of the mask material 200, wherein the pores 226 extend through the elastomeric material.

Figure 2:
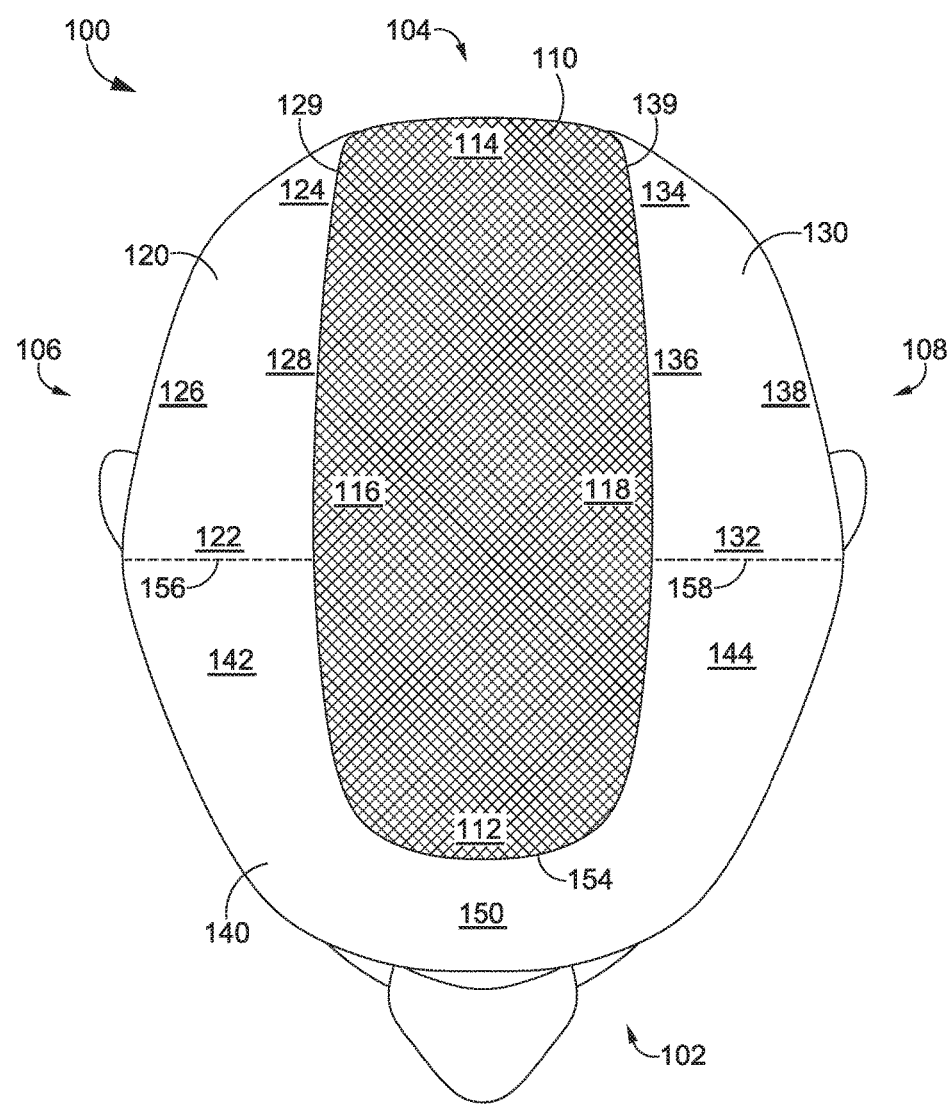
FIG. 2 depicts a top plan view of the exemplary cooling headgear of FIG. 1 in accordance with aspects herein.

FIG. 2 illustrates a top plan view of cooling headgear 100 in accordance with aspect herein. FIG. 2 depicts the anterior aspect 102, the right portion aspect 106, a left portion aspect 108, and a posterior aspect 104. As described, the vent panel 110 has an anterior portion 112, the posterior portion 114, the right side 116, and the left side 118. In one exemplary aspect, the vent panel 110 may be oblong with a rounded anterior portion 112 which tapers to a squared off posterior portion 114. However, other configurations of the vent panel 110 are possible. The vent panel 110 may be oriented to lie over the top and back of a user's head when the headgear 100 is worn. As shown in FIG. 2, the vent panel 110 is attached to the right panel 120, a left panel 130, and the face panel 140. The right side 116 of the vent panel 110 is attached to the superior side 128 of the right panel 120 at seam 129. The left side 118 of the vent panel 110 is attached to the superior side 136 of the left panel 130 at seam 139. Attachment of the panels may be accomplished by any of the affixing technologies mentioned above. In exemplary aspects, the vent panel 110 may be comprised of the porous material described above and shown in FIG. 7.

Figure 3:
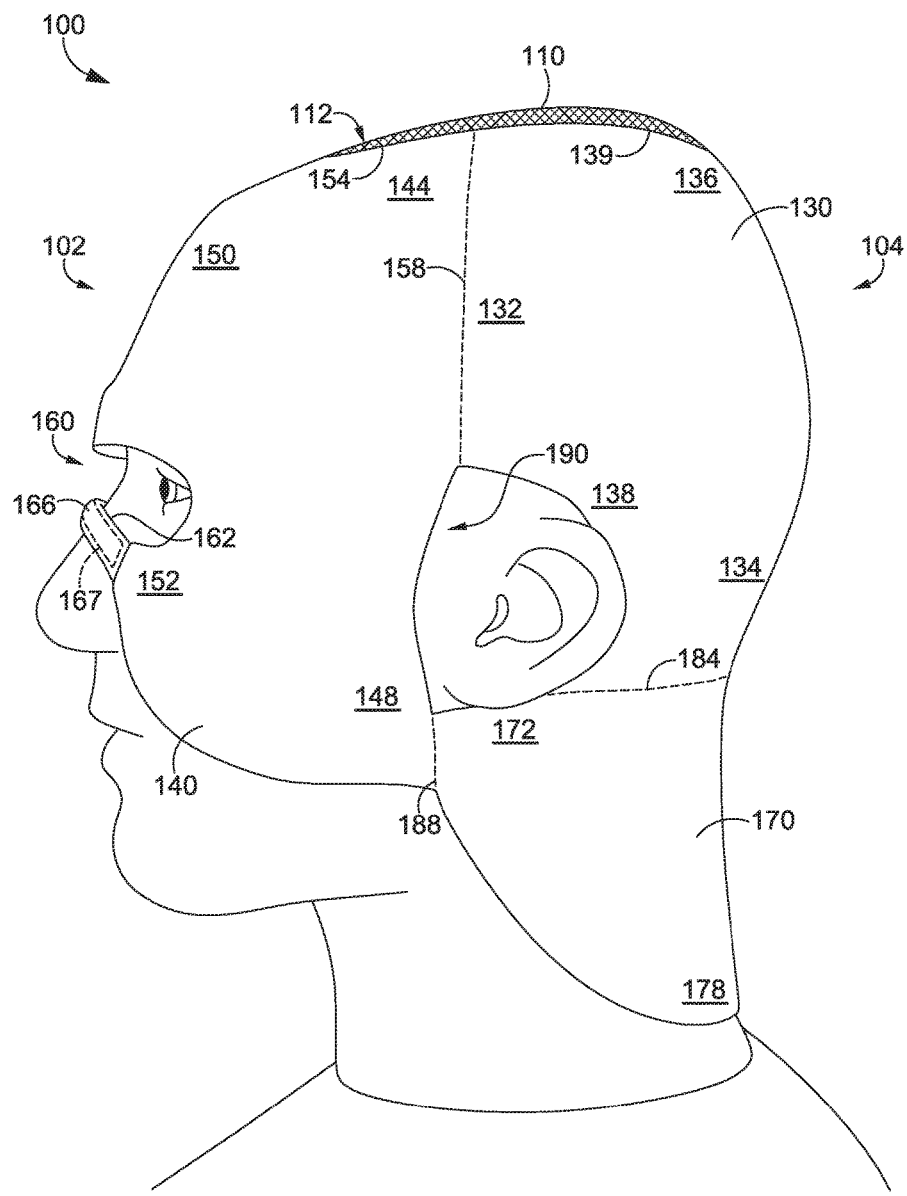
FIG. 3 depicts a right side view of the exemplary cooling headgear of FIG. 1 in accordance with aspects herein.

A side elevation view of the left portion aspect 108 of the exemplary cooling headgear 100 is shown in FIG. 3 in accordance with aspects herein. The left panel 130 comprises an anterior portion 132, a posterior portion 134, the superior side 136, and an inferior side 138. The left panel 130 may have an oblong, rectangular shape having a C-shaped indentation at the inferior side 138. Other configurations are possible. The left panel 130 may be comprised of the mask material 200 described above. As shown in FIG. 3, the left panel 130 is attached to the vent panel 110, the face panel 140, and the neck panel 170. For instance, the anterior portion 132 of the left panel 130 is attached to the left superior portion 144 of the face panel 140 at seam 158. The posterior portion 134 of the left panel 130 is attached to the left superior portion 172 of the neck panel 170 at seam 184. Attachment may be accomplished by any of the exemplary affixing technologies listed above.

The left inferior portion 148 of the face panel 140 may be attached to the left superior portion 172 of the neck panel 170 at seam 188 to form an optional left ear opening 190. The ear opening 190 may be generally circular in shape and is configured to allow a user's ear to remain uncovered by the headgear 100. Alternatively, the ear opening 190 may be covered with the porous material described above. Attachment may be made by any of the affixing technologies listed above. Alternatively, seam 188 may be affixed using a fastener, as described above.

Figure 4A:
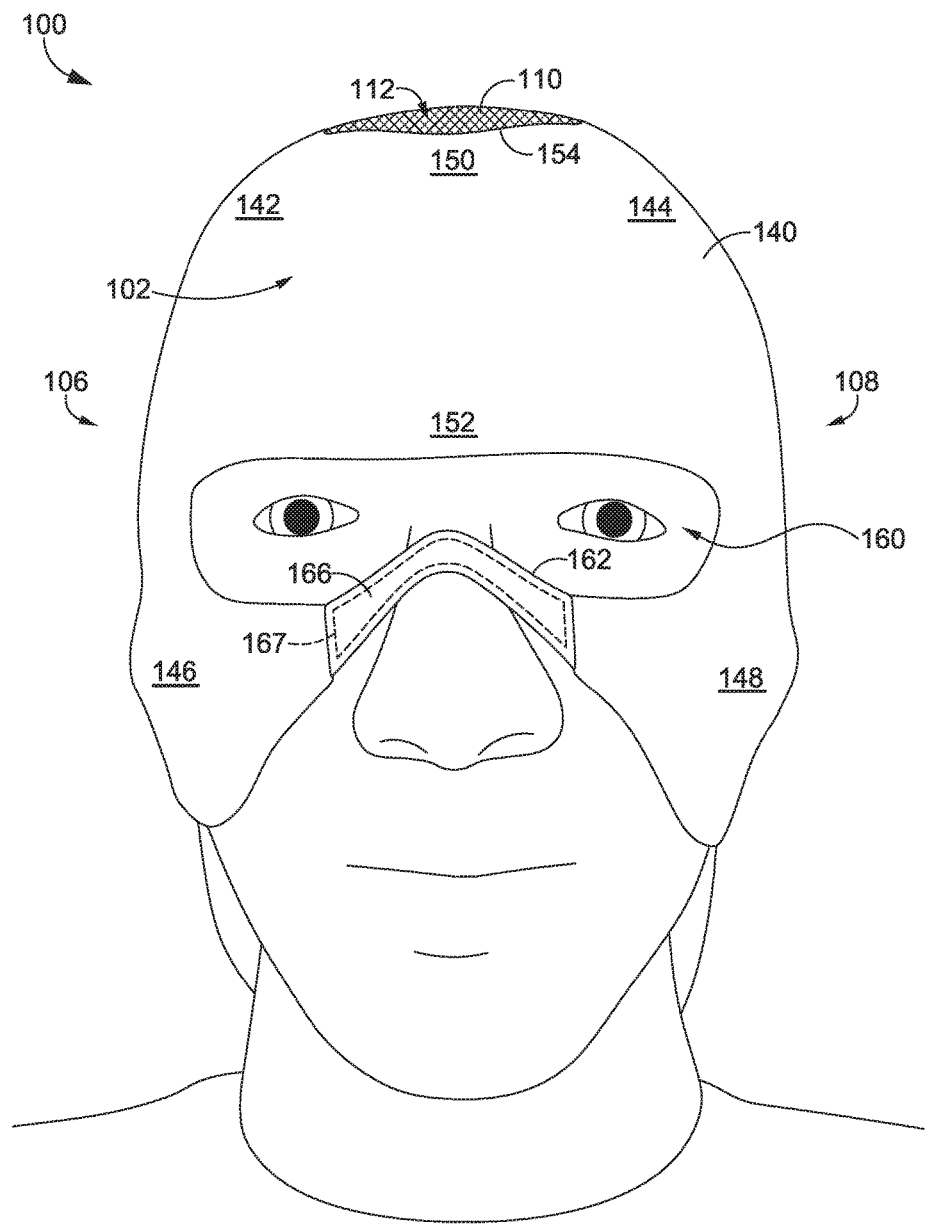
FIG. 4A depicts a front view of the exemplary cooling headgear of FIG. 1 in accordance with aspects herein.

FIG. 4A illustrates a front elevation view of the anterior aspect 102 of the exemplary cooling headgear 100 in accordance with aspects herein. The face panel 140 comprises a right superior portion 142, a left superior portion 144, a right inferior portion 146, a left inferior portion 148, a center superior portion 150, and a center inferior portion 152. The face panel 140 may be in a modified rectangular shape wherein the center is compressed compared to the right and left ends. Other configurations are possible. The face panel 140 may be comprised of the mask material 200 described above. The center superior portion 150 of the face panel 140 is attached to the anterior portion 112 of the vent panel 110 at seam 154. The face panel 140 is designed to curve around and conform to a user's face, covering the user's forehead and upper cheeks when worn, but leaving the user's nose and mouth exposed.

Figure 4B:
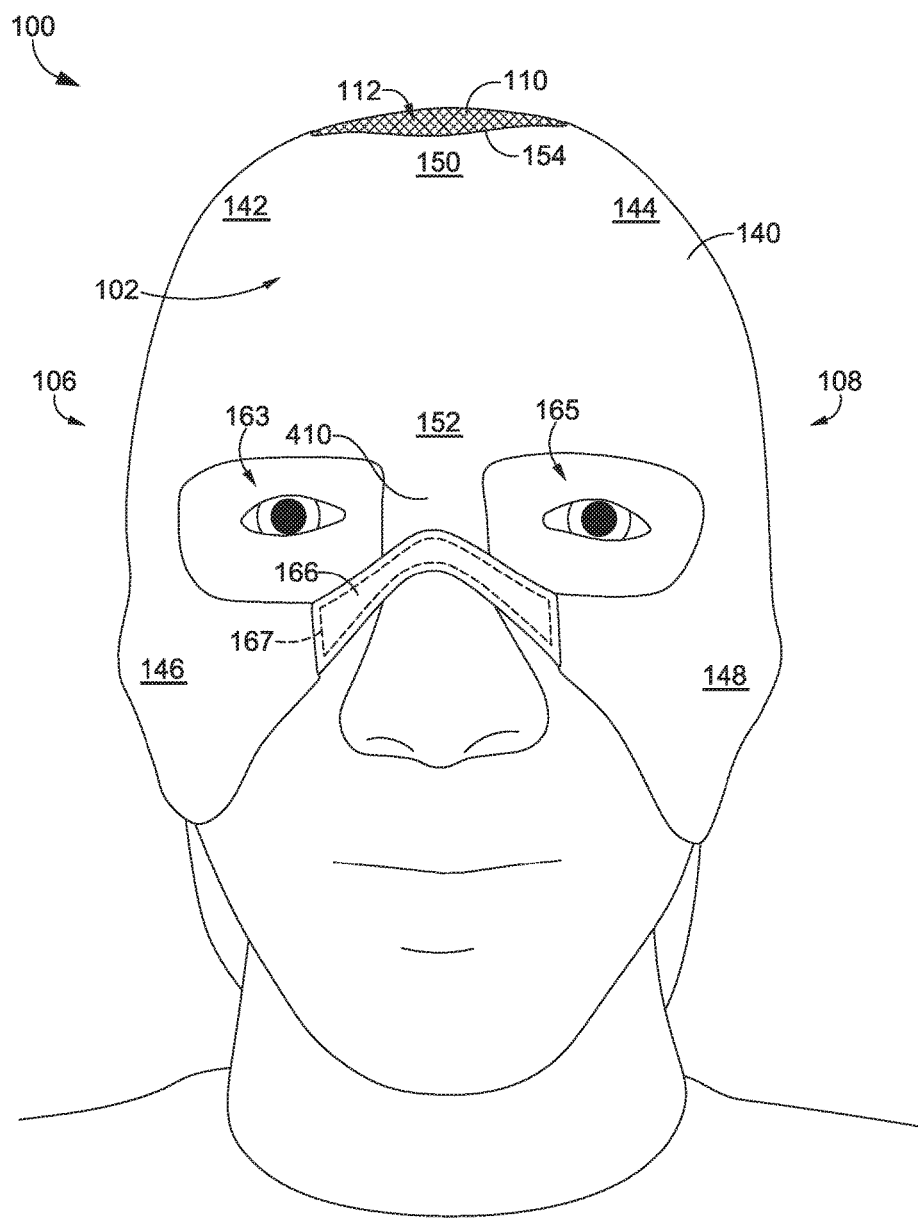
FIG. 4B depicts a front elevation view of an alternative exemplary cooling headgear in accordance with aspects herein.

FIG. 4B illustrates a front elevation view of the anterior aspect 102 of an alternative configuration for the cooling headgear 100, wherein the eye opening 160 comprises a right eye hole 163 and a left eye hole 165 separated by a piece of material 410 adapted to cover in part a user's nose when the headgear 100 is worn.

Figure 5:
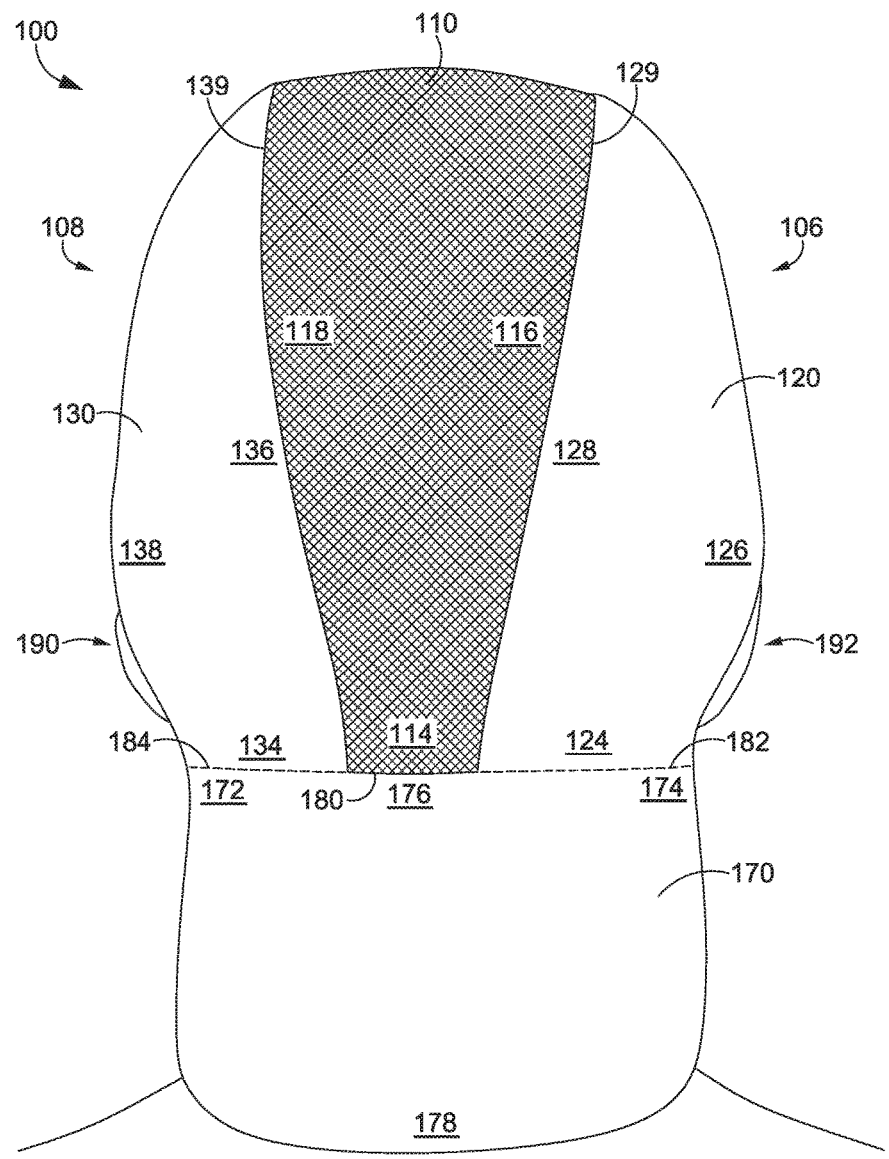
FIG. 5 depicts a rear view of the exemplary cooling headgear of FIG. 1 in accordance with aspects herein.

A back elevation view of the posterior aspect 104 of the cooling headgear 100 is shown in FIG. 5 in accordance with aspects herein. The neck panel 170 has the left superior portion 172, the right superior portion 174, a center superior portion 176, and the inferior portion 178, as shown in FIG. 5. The neck panel 170 has a shape similar to a semicircle. However, other shapes and configurations are possible. The neck panel 170 is comprised of the mask material 200 described above. The neck panel 170 is designed to hang over and cover a user's neck when the headgear 100 is worn. The center superior portion 176 of the neck panel 170 is attached to the posterior portion 114 of the vent panel 110 at seam 180, as shown in FIG. 5. The right superior portion 174 of the neck panel 170 is attached to the posterior portion 124 of the right panel 120 at seam 182. The left superior portion 172 of the neck panel 170 is attached to the posterior portion 134 of the left panel 130 at seam 184. Attachments at the seams may be made by any of the affixing technologies mentioned above.

Figure 8:
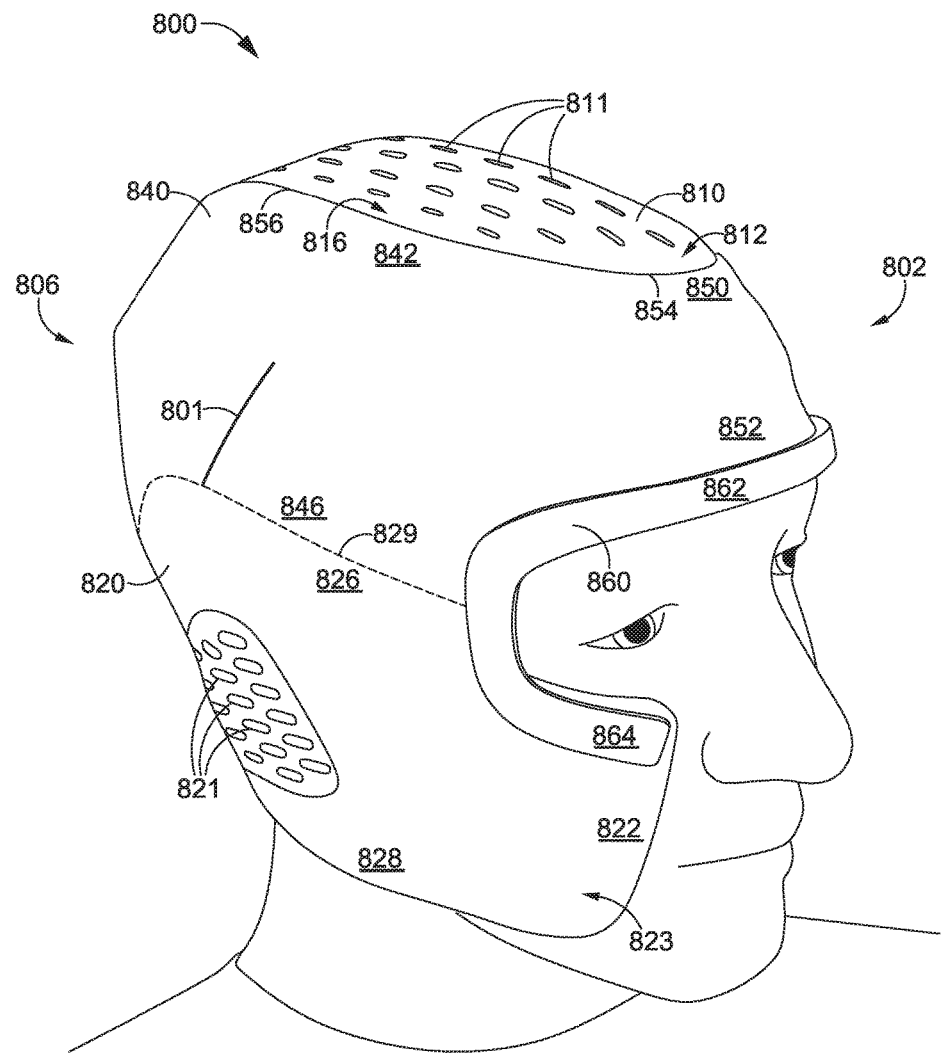
FIG. 8 depicts a front perspective view of an exemplary cooling headgear as worn by a user in accordance with aspects herein.

Turning now to FIG. 8, a front perspective view of another exemplary cooling headgear 800 is illustrated. The cooling headgear 800 may be worn over the head of a user, as shown. FIG. 8 depicts an anterior aspect 802 and a right portion aspect 806 of the cooling headgear 800. As shown, the cooling headgear 800 comprises a superior panel 840, a vent panel 810, and a right inferior panel 820. The headgear 800 further comprises a left inferior panel 830 which is not shown because of the perspective view of FIG. 1. The right inferior panel 820 further comprises an anterior region 822, a superior region 826, and an inferior region 828. The superior panel 840 comprises a right superior region 842, a right inferior region 846, a center superior region 850, and a center inferior region 852. As shown in FIG. 8, the vent panel 810 comprises an anterior region 812, a right side 816, and a left side (not shown in FIG. 1). The vent panel 810, the right inferior panel 820, the left inferior panel 830, and the superior panel 840 may be comprised of the mask material 200 discussed in relation to FIG. 6.

With respect to FIG. 8, the right superior region 842 of the superior panel 840 is attached to the right side 816 of the vent panel 810 at a seam 856. The center superior region 850 of the superior panel 840 is attached to the anterior region 812 of the vent panel 810 at a seam 854. The seam 854 may comprise an extension of the seam 856. The superior region 826 of the right inferior panel 820 is attached to the right inferior region 846 of the superior panel 840 at a seam 829. In an optional aspect, one or more darts 801 may be used to ensure that the cooling headgear 800 fits snugly against the user's head when worn. Attachments between the panels of the cooling headgear 800 at the various seams may be accomplished by a number of affixing technologies including stitching, bonding, or otherwise affixing the materials together. In an exemplary aspect, the panels are joined by bonding the seams together with adhesive film. An exemplary adhesive film is Sewfree® 3415 produced by Bemis.

The cooling headgear 800 may also include an eye opening structure 860, as shown in FIG. 8 and FIGS. 11A-11E. The eye opening structure 860 is located proximate to the center inferior region 852 of the superior panel 840. A superior portion 862 of the eye opening structure 860 is attached to the center inferior region 852 of the superior panel 840 by various affixing technologies discussed herein (e.g., bonding, stitching, snap closures, adhesive, hook-and-loop fasteners, and the like). The right inferior portion 864 of the eye opening structure 860 extends down and around of a user's eye area in a "C" shape and is attached to the anterior region 822 of the right inferior panel 820. The eye opening structure 860 is positioned such that a user's eyes are not obstructed while wearing the headgear 800. The eye opening structure 860 helps to secure the anterior region 822 of the right inferior panel 820 against the user's cheek, positioning the right cheek flap 823 over the user's face. The right cheek flap 823 helps to cool the user's face, but leaves the user's nose, mouth, and lower cheek exposed. This is beneficial as the headgear 800 will cover much of the user's face to provide cooling, but does not obstruct vision or breathing. Further, the cheek flaps 823 may be designed such that they leave the lower cheeks exposed for users with beards. The eye opening structure 860 is comprised of rigid material, which may be formed of plastic by injection molding, 3D printing, or similar techniques. Exemplary materials may comprise plastic, rubber, metal, polyurethane, thermoplastic polyurethane, and the like. The eye opening structure 860 is formed to have a curved shape conforming to the contours of a user's face. The eye opening structure 860 may be permanently or removably affixed to the cooling headgear 800. For instance, a user may wish to remove the eye opening structure 860 to wash the headgear, douse the headgear 800 in water, or store the headgear 800. The eye opening structure 860 may be removably affixed to the headgear 800 with fastening means such as hook-and-loop fasteners, snaps, magnets, and the like.

The right inferior panel 820 may include a plurality of ear openings 821 that are preferably aligned with a user's ear to allow for flow of air and to prevent the user's hearing from being muffled. In exemplary aspects, the ear openings 821 extend through all of the layers of the mask material 200 comprising the right inferior panel 820. Alternatively, the ear openings 821 may comprise a single large opening for the user's ear, thus completely exposing the user's ear when the headgear 800 is in use. In another exemplary aspect the ear area may be covered with a porous material, such as the porous material 220 of FIG. 7, rather than mask material 200.

Figure 9:
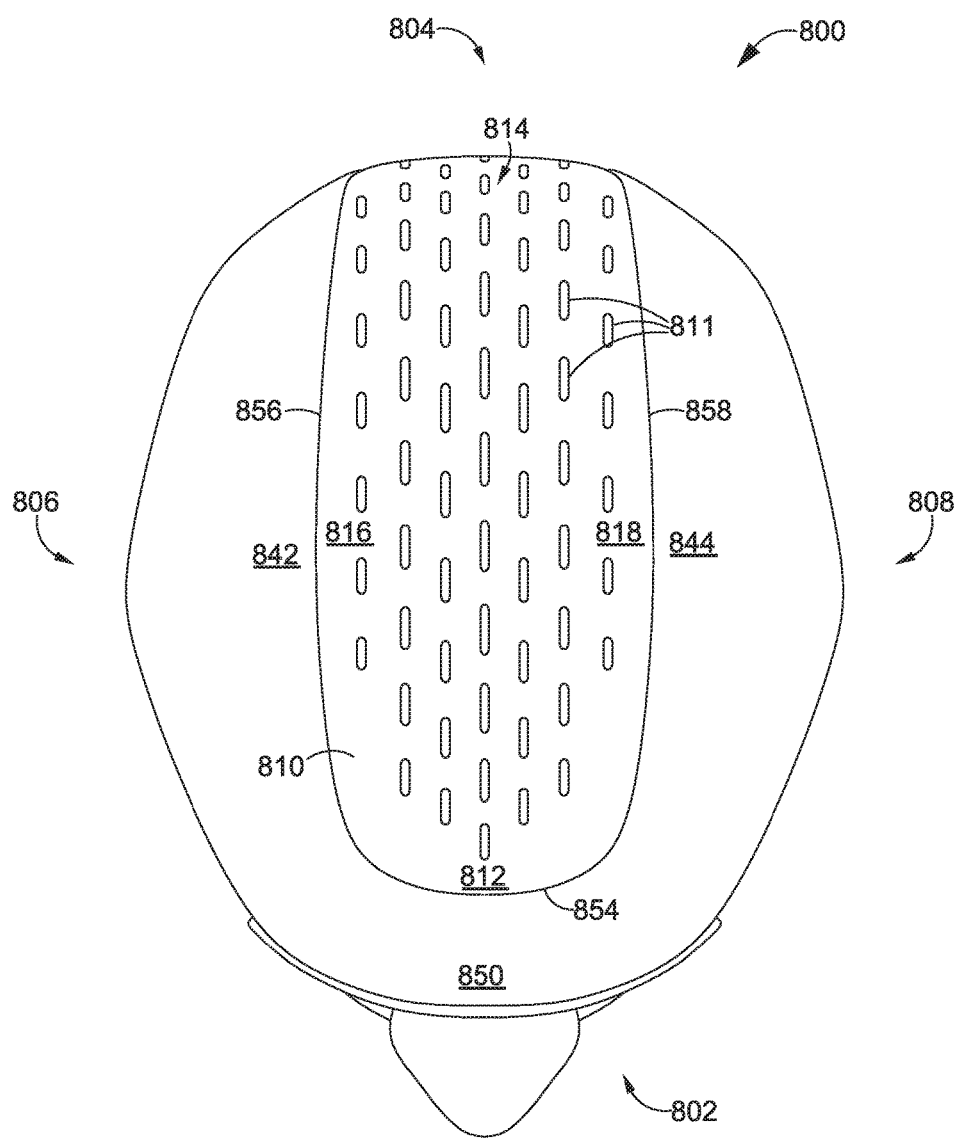
FIG. 9 depicts a top plan view of the exemplary cooling headgear of FIG. 8 in accordance with aspects herein.

FIG. 9 illustrates a top plan view of the cooling headgear 800, showing the anterior aspect 802, the right portion aspect 806, a left portion aspect 808, and a posterior aspect 804. The vent panel 810 has an anterior region 812, a posterior region 814, a right side 816, and a left side 818. The vent panel 810 may be oriented to lie over the top and back of a user's head when the headgear 800 is worn. As shown in FIG. 9, the vent panel 810 is attached to the superior panel 840. In particular, the right side 816 of the vent panel 810 is attached to the right superior region 842 of the superior panel 840 at seam 856. The left side 818 of the vent panel 810 is attached to the left superior region 844 of the superior panel 840 at seam 858. The seam 858 may comprise an extension of the seam 856. Attachment of the panels may be accomplished by any of the affixing technologies mentioned above. The vent panel 810 may be comprised of the porous material 220 described above and shown in FIG. 7. Alternatively, the vent panel 810 may be comprised of the mask material 200 shown in FIG. 6 and may comprise a plurality of apertures 811. The apertures 811 extend through all of the layers of the mask material 200, allowing air to move through the material freely. Any and all such aspects, and any variation thereof, are contemplated as being within the scope herein.

Figure 10:
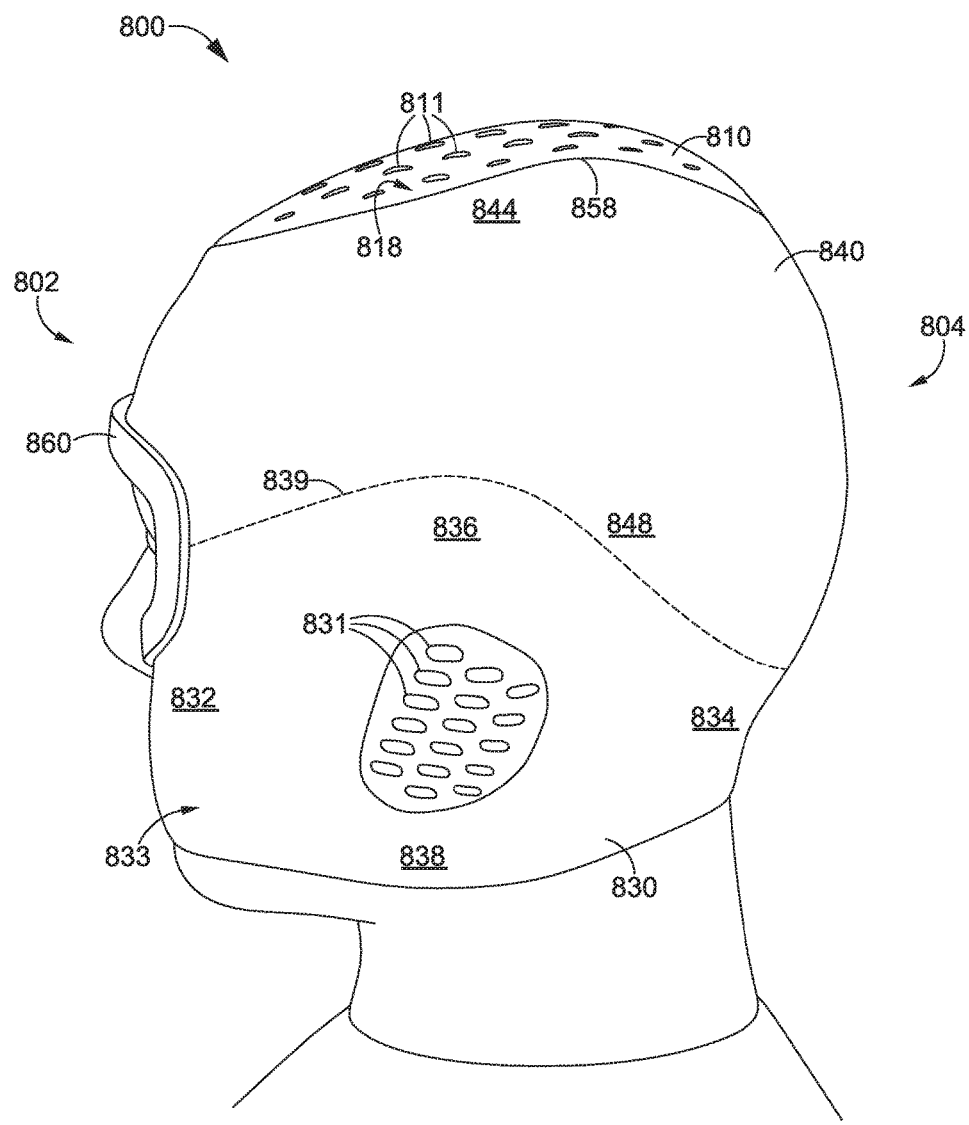
FIG. 10 depicts a left side view of the exemplary cooling headgear of FIG. 8 in accordance with aspects herein.

A side elevation view of the left side of the exemplary cooling headgear 800 is shown in FIG. 10. The left inferior panel 830 has an anterior region 832, a posterior portion 834, a superior region 836, and an inferior region 838. The left inferior panel 830 may be comprised of the mask material 200 described above. As shown in FIG. 10, the superior region 836 of the left inferior panel 830 is attached to the left inferior region 848 of the superior panel 840 at seam 839. The left superior region 844 of the superior panel 840 is attached to the left side 818 of the vent panel 810 at a seam 858. Attachment may be accomplished by any of the exemplary affixing technologies listed above. The anterior region 832 of the left inferior panel 830 is unattached, forming a left cheek flap 833. The left cheek flap 833 may be held in place by the eye opening structure 860 as described above. The left inferior panel 830 may include a plurality of ear openings 831. As described above, the ear openings 831 may comprise a plurality of apertures extending through the mask material 200 as shown, or the ear openings 831 may comprise a single large opening exposing the user's ear. In another exemplary aspect, the ear area may be covered with a porous material, such as the porous material 220 of FIG. 7, rather than mask material 200.

Figure 11A:
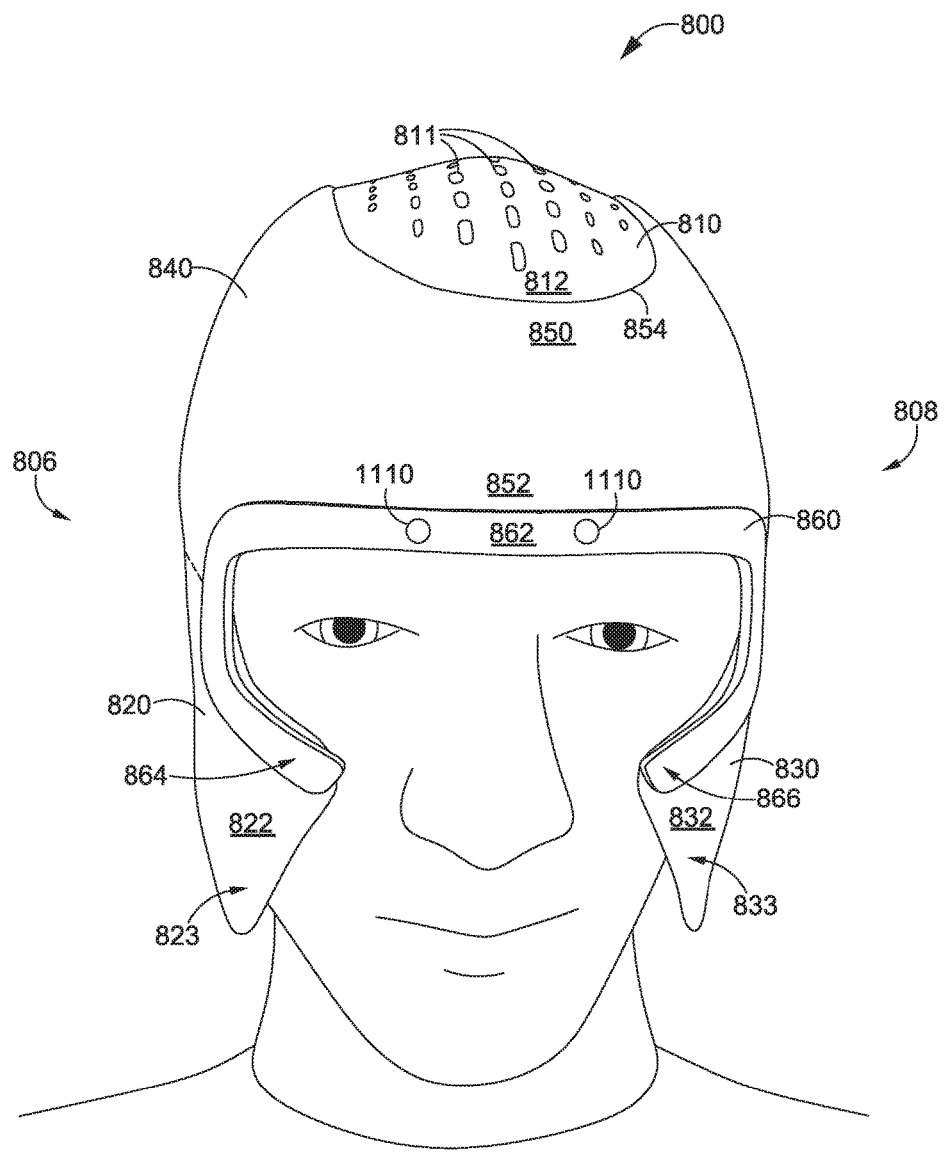
FIGS. 11A-11E depict front elevation views of some alternative configurations for the exemplary cooling headgear of FIG. 8 in accordance with aspects herein.

FIG. 11A illustrates a front elevation view of the anterior aspect 802 of the exemplary cooling headgear 800 in accordance with aspects herein. The center superior region 850 and center inferior region 852 of the superior panel 840 are visible, as is the anterior region 812 of the vent panel 810. The superior panel 840 may be comprised of the mask material 200 described above. The center superior region 850 of the superior panel 840 is attached to the anterior region 812 of the vent panel 810 at seam 854. The center inferior region 852 of the superior panel 840 is attached to the superior portion 862 of the eye opening structure 860. The attachment may be permanent or removable. The superior panel 840 is designed to curve around a user's head, covering the user's forehead and wrapping around to the back of the user's head where it meets the vent panel 810 when the headgear 800 is worn.

The eye opening structure 860 extends down and around a user's eye sockets forming a right inferior portion 864 and left inferior portion 866. The right inferior portion 864 is attached to the anterior region 822 of the right inferior panel 820, helping to secure the right cheek flap 823 over the user's cheek area. Similarly, the left inferior portion 866 of the eye opening structure 860 is attached to the anterior region 832 of the left inferior panel 830 helping to secure the left cheek flap 833 over the user's cheek area. Securing the cheek flaps 823 and 833 in this way helps to prevent the flaps 823 and 833 from moving during activity and potentially distracting the user. In another exemplary configuration, and as shown in FIG. 11D, the cheek flaps 823 and 833 may be configured such that they do not extend as far inferiorly thus covering less of the user's face when the cooling headgear 800 is worn.

Continuing, in an exemplary aspect, the eye opening structure 860 may comprise optional magnets 1110 embedded in the material forming the eye opening structure 860. As explained below, the magnets 1110 may be used to removably affix a pair of eyeglass frames to the cooling headgear 800.

Figure 11B:
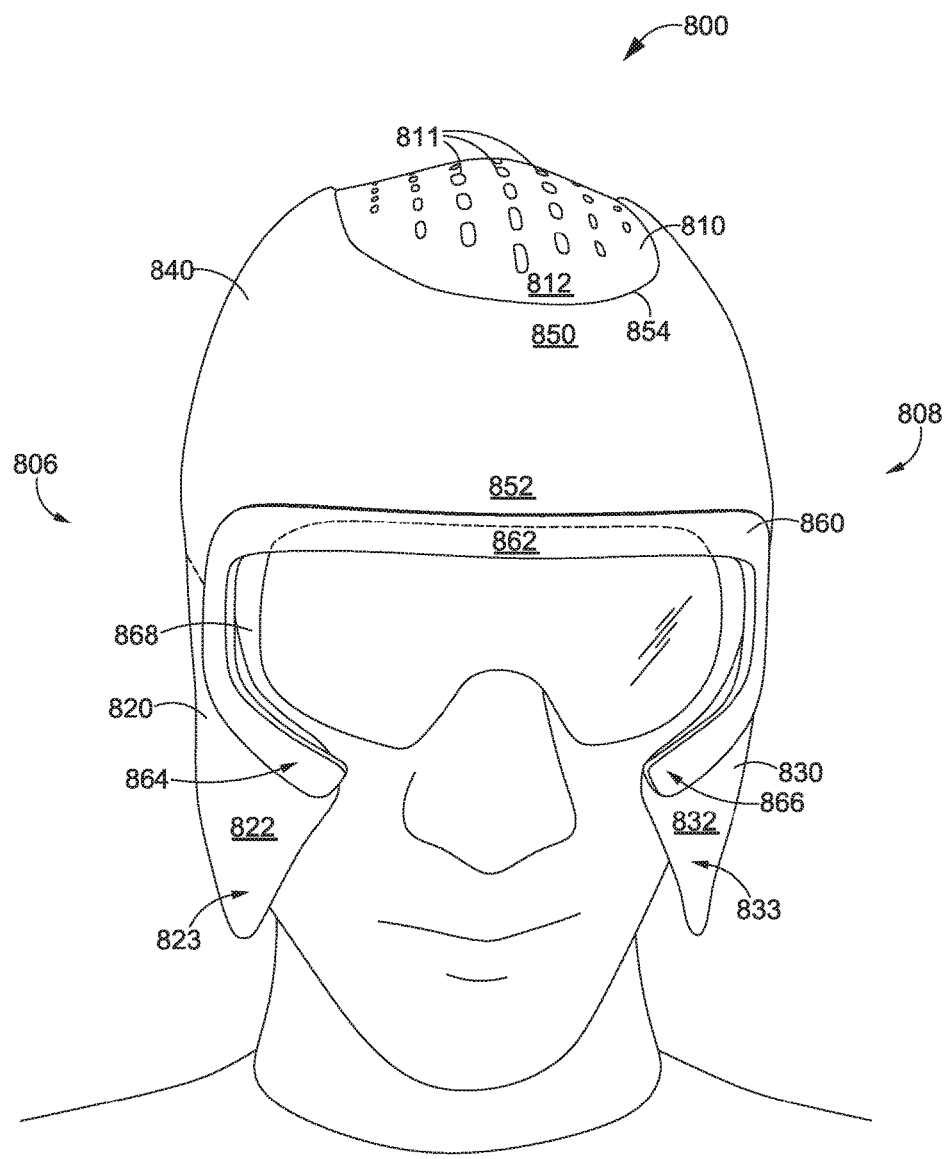
Figure 11C:
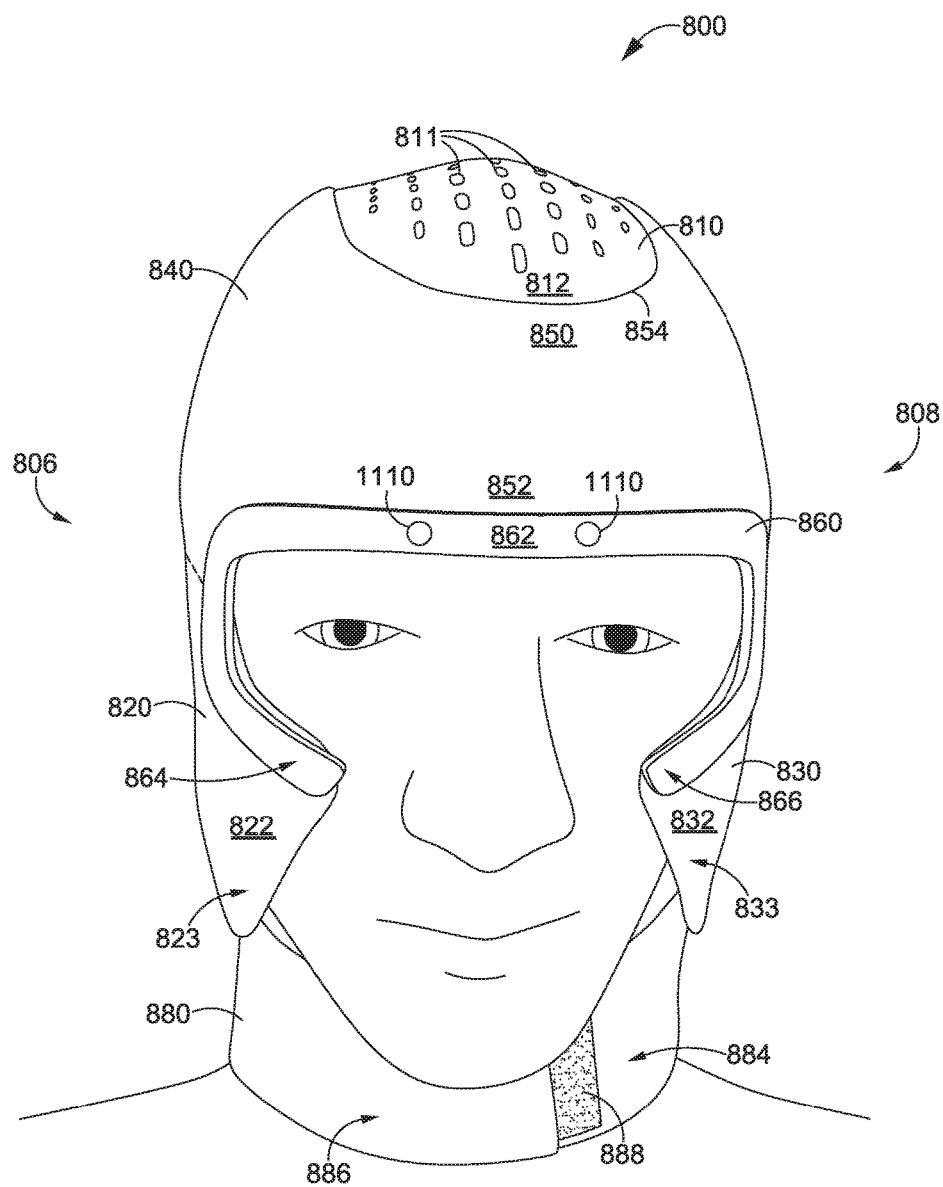
Figure 11D:
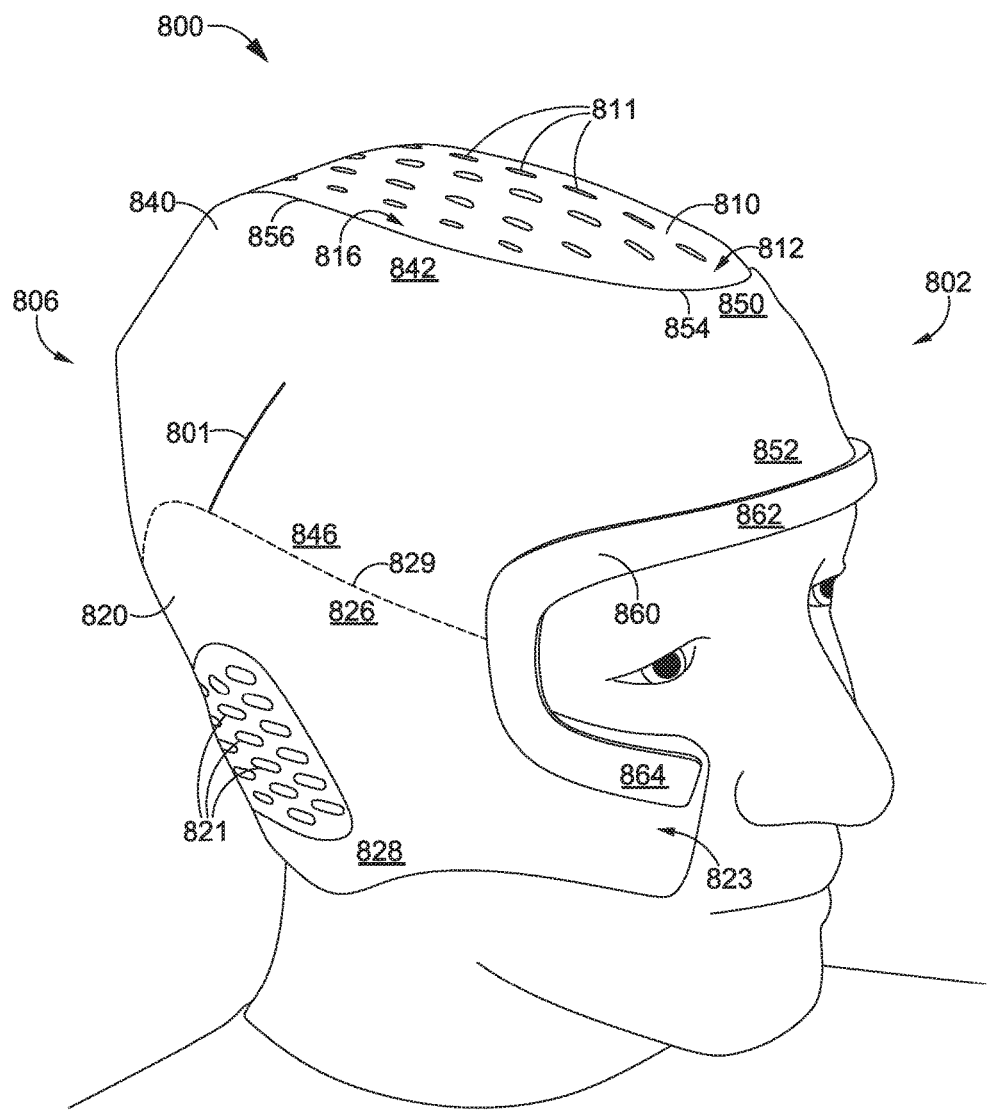
Figure 11E:
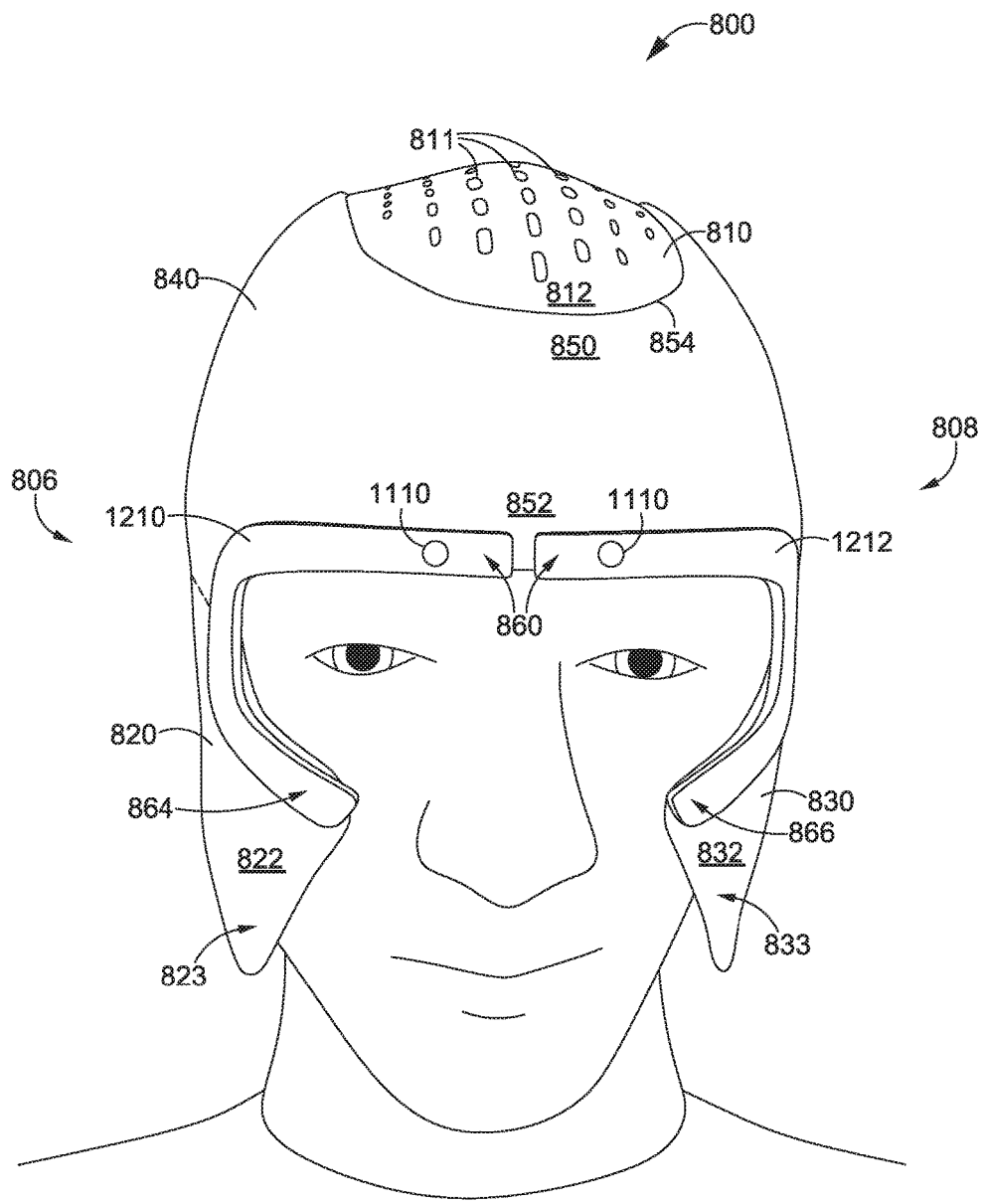

In exemplary aspects, the eye opening structure 860 may comprise two separate elements as shown in FIG. 11E. As shown in FIG. 11E, the eye opening structure 860 comprises a first element 1210 and a second element 1212 that are positioned on the cooling headgear 800 such that the superior terminal ends of each are adjacent to each other. By using two separate elements 1210 and 1212, the eye opening structure 860 may be used on headgears of different sizes.

Turning now to FIG. 11B, FIG. 11B illustrates a front elevation view of the anterior aspect 802 of an alternative configuration for the cooling headgear 800, wherein sunglasses 868 are placed within the eye opening structure 860. In one example, the sunglasses 868 do not have temple portions and the frame and lenses (or just the lenses) are removably affixed to the eye opening structure 860 with magnets, snaps, slots, tabs, ridges, or similar affixing means. For example, the magnets 1110 located on the eye opening structure 860 may mate with opposite pole magnets located on the sunglasses 868. The sunglasses 868 may then be removably attached to the eye opening structure 860 via the magnets 1110. Alternatively, the eye opening structure 860 may be designed to allow enough room for a user to wear sunglasses underneath the cooling headgear 800.

FIG. 11C illustrates a front elevation view of another example of the cooling headgear 800 having a cooling collar 880. The cooling collar 880 may be removably or permanently attached at the posterior aspect 804 of the cooling headgear 800, as shown in FIG. 12C, which is described below. The left flap 884 and right flap 886 of the cooling collar 880 are visible. In exemplary aspects, the right flap 886 overlaps the left flap 884 and is joined at the front of the user's neck using a fastener 888. However, it is contemplated herein that the left flap 884 may overlap the right flap 886. The fastener 888 may comprise hook-and-loop fasteners, snaps, buttons, and the like. The cooling collar 880 may be comprised of the mask material 200 of FIG. 6. The cooling collar 880 functions to further cool a user by holding cool water against the neck of the user.

Figure 12A:
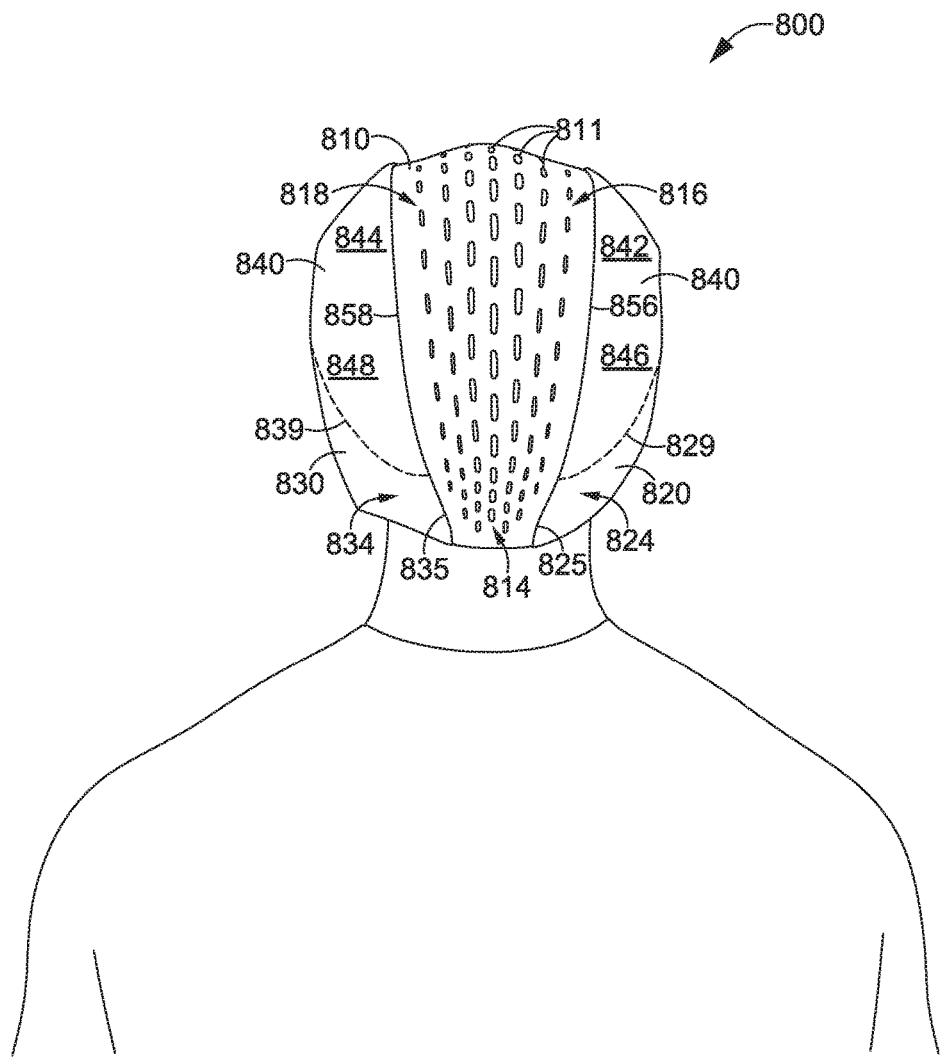
FIG. 12A depicts a rear elevation view of an exemplary cooling headgear as worn by a user in accordance with aspects herein.

A back elevation view of the posterior aspect 804 of the cooling headgear 800 is shown in FIG. 12A. The posterior region 814, right side 816, and left side 818 of the vent panel 810 are visible. The posterior region 814 of the vent panel 810 ends at the base of the user's head when the cooling headgear 800 is worn. In other words, the posterior region 814 of the vent panel 810 forms an inferior margin of the cooling headgear 800. As previously mentioned, the vent panel 810 may have a plurality of apertures 811 to provide ventilation. The left superior region 844 of the superior panel 840 is connected to the left side 818 of the vent panel 810 at seam 858. The right superior region 842 of the superior panel 840 is connected to the right side 816 of the vent panel 110 at seam 856. The posterior portion 824 of the right inferior panel 820 is joined to the posterior region 814 of the vent panel 810 at seam 825. The posterior portion 834 of the left inferior panel 830 is joined to the posterior region 814 of the vent panel 810 at seam 835. The left inferior region 848 of the superior panel 840 is attached to the posterior portion 834 of the left inferior panel 830 at seam 839. The right inferior region 846 of the superior panel 840 is attached to the posterior portion 824 of the right inferior panel 820 at seam 829.

Figure 12B:
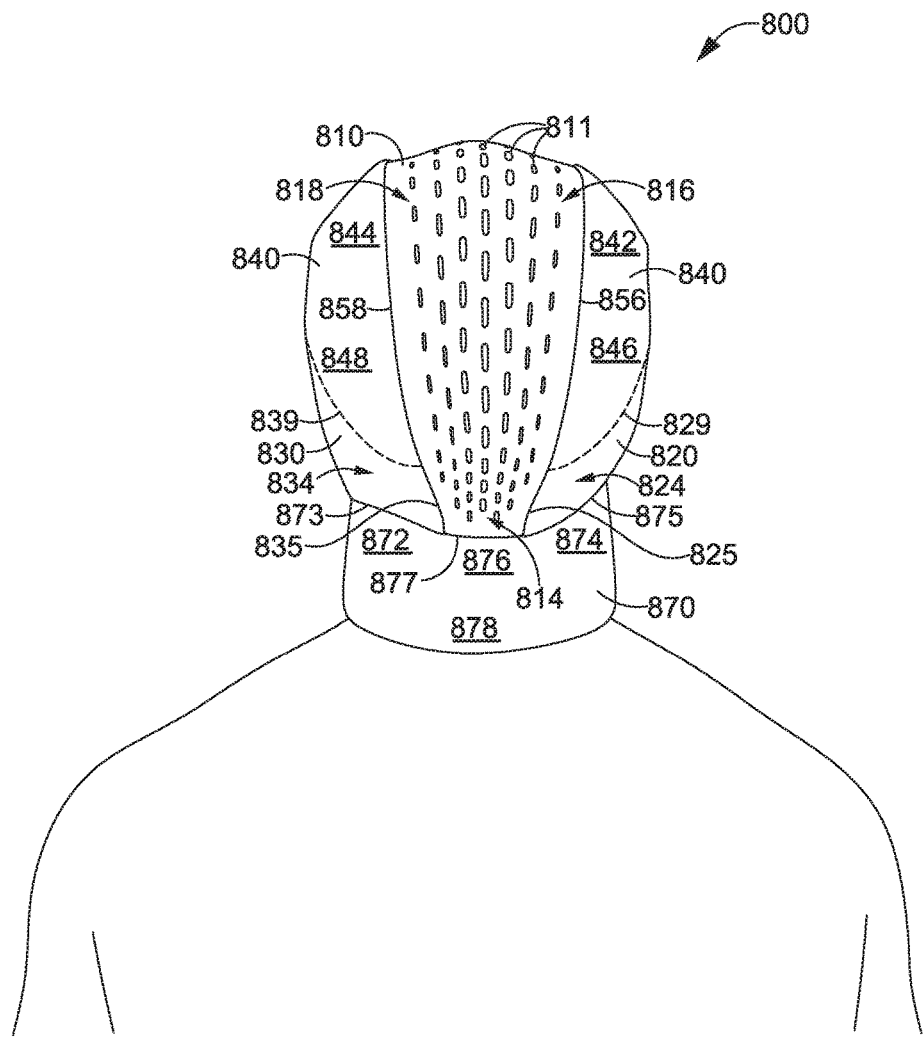
FIG. 12B depicts a rear elevation view of an alternative exemplary implementation of a cooling headgear having a cooling collar in accordance with aspects herein.
Figure 12C:
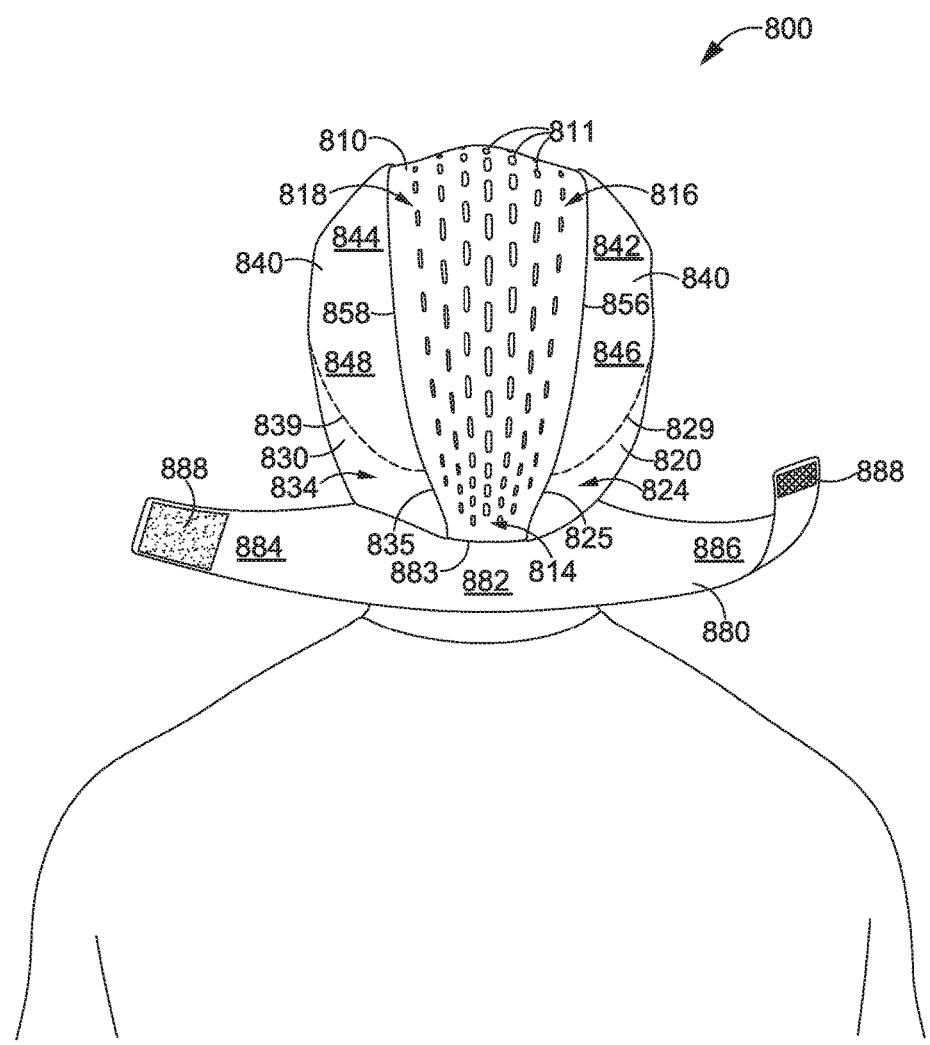
FIG. 12C depicts a rear elevation view of the alternative exemplary implementation of the cooling headgear of FIG. 12B in accordance with aspects herein.

FIG. 12B illustrates another example of the cooling headgear 800 having a neck panel 870. The neck panel 870 has a left superior region 872, a right superior region 874, a center superior region 876, and an inferior region 878. The neck panel 870 is comprised of the mask material 200 described above. The neck panel 870 is designed to hang over and cover a user's neck when the cooling headgear 800 is worn. The center superior region 876 of the neck panel 870 is attached to the posterior region 814 of the vent panel 810 at seam 877, as shown in FIG. 12B. The right superior region 874 of the neck panel 870 is attached to the posterior portion 824 of the right inferior panel 820 at seam 875. The seam 875 may comprise an extension of the seam 877. The left superior region 872 of the neck panel 870 is attached to the posterior portion 834 of the left inferior panel 830 at seam 873. The seam 873 may comprise an extension of the seams 875 and 877. Attachments at the seams may be made by any of the affixing technologies mentioned above.

FIG. 12C illustrates a back elevation view of the exemplary cooling headgear 800 of FIG. 11C having the cooling collar 880 instead of the neck panel 870 in accordance with aspects herein. The cooling collar 880 has a center region 882, the left flap 884, and the right flap 886. In this view, the flaps 884 and 886 of the cooling collar 880 are unattached and are extended outward. As mentioned above, the cooling collar 880 is comprised of mask material 200. The center region 882 of the cooling collar 880 is attached to the posterior portion 824 of the right inferior panel 820, the posterior portion 834 of the left inferior panel 830, and the posterior region 814 of the vent panel 810 at a seam 883. The left flap 884 and right flap 886 extend in opposite directions away from the center region 882 of the cooling collar 880. The left flap 884 and right flap 886 are configured to wrap around a user's neck and may be fastened at the front of the user's neck with the fastener 888, as shown in FIG. 11C. The fastener 888 may be any of a number of reversible attachment mechanisms including, for example, hook-and-loop fasteners, buttons, snaps, buckles, clips, clasps, or hook-and-eye fasteners.

Figure 12D:
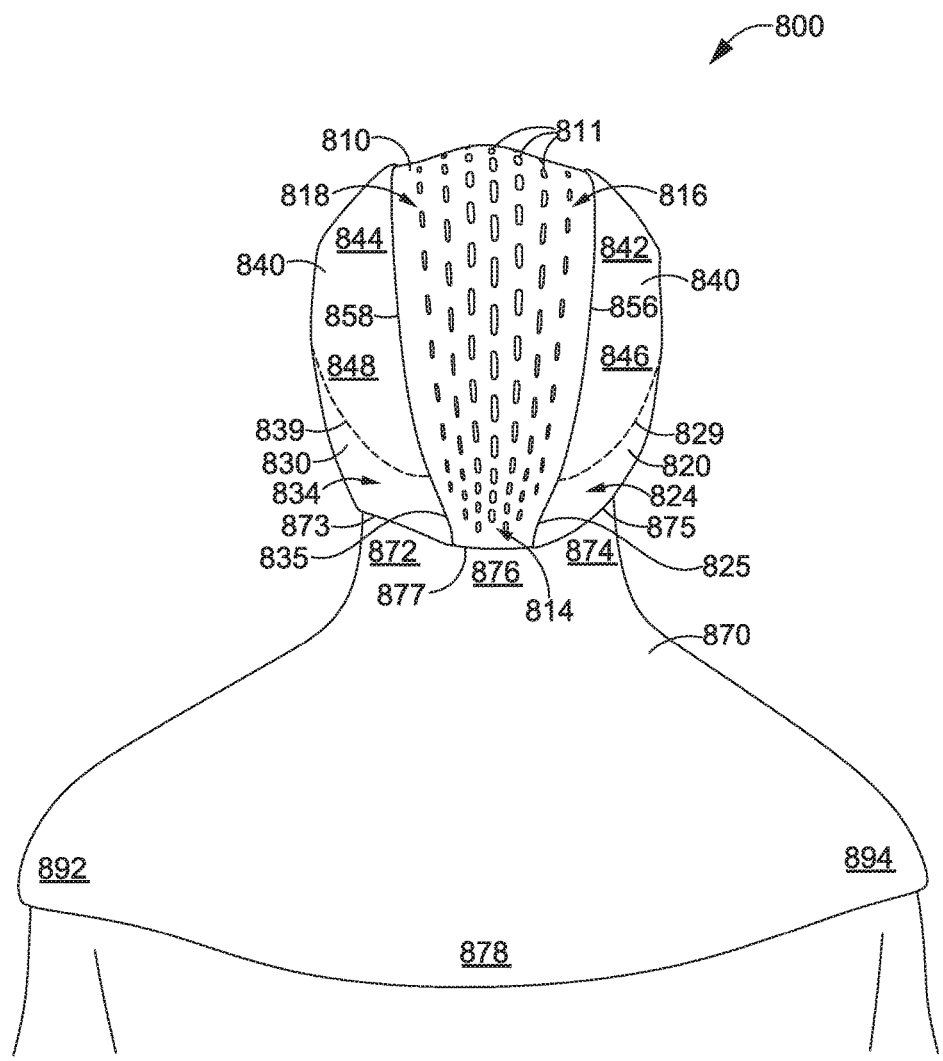
FIG. 12D depicts a rear elevation view of an alternative exemplary implementation of a cooling headgear in accordance with aspects herein.

FIG. 12D illustrates another example of the cooling headgear 800 wherein a neck panel 870 is extended to cover the user's shoulders. The center superior region 876 of the neck panel 870 may be removably or permanently attached to the posterior region 814 of the vent panel 810 at seam 877. The right superior region 874 of the neck panel 970 is attached to the posterior portion 824 of the right inferior panel 820 at seam 875. The left superior region 872 of the neck panel 870 is attached to the posterior portion 834 of the left inferior panel 830 at seam 873. The inferior region 878 of the neck panel 870 extends down the back of the user when the cooling headgear 800 is worn. For instance, a left shoulder extension 892 is adapted to extend to cover the left shoulder of a user, and a right shoulder extension 894 is adapted to extend to cover the right shoulder of a user. The neck panel 870 may be comprised of mask material 200 which may be soaked in cool water when in use. The neck panel 870 in FIG. 12D is adapted to cover a greater surface area of the body of a user, thus providing further cooling relief to the user.

Figure 12E:
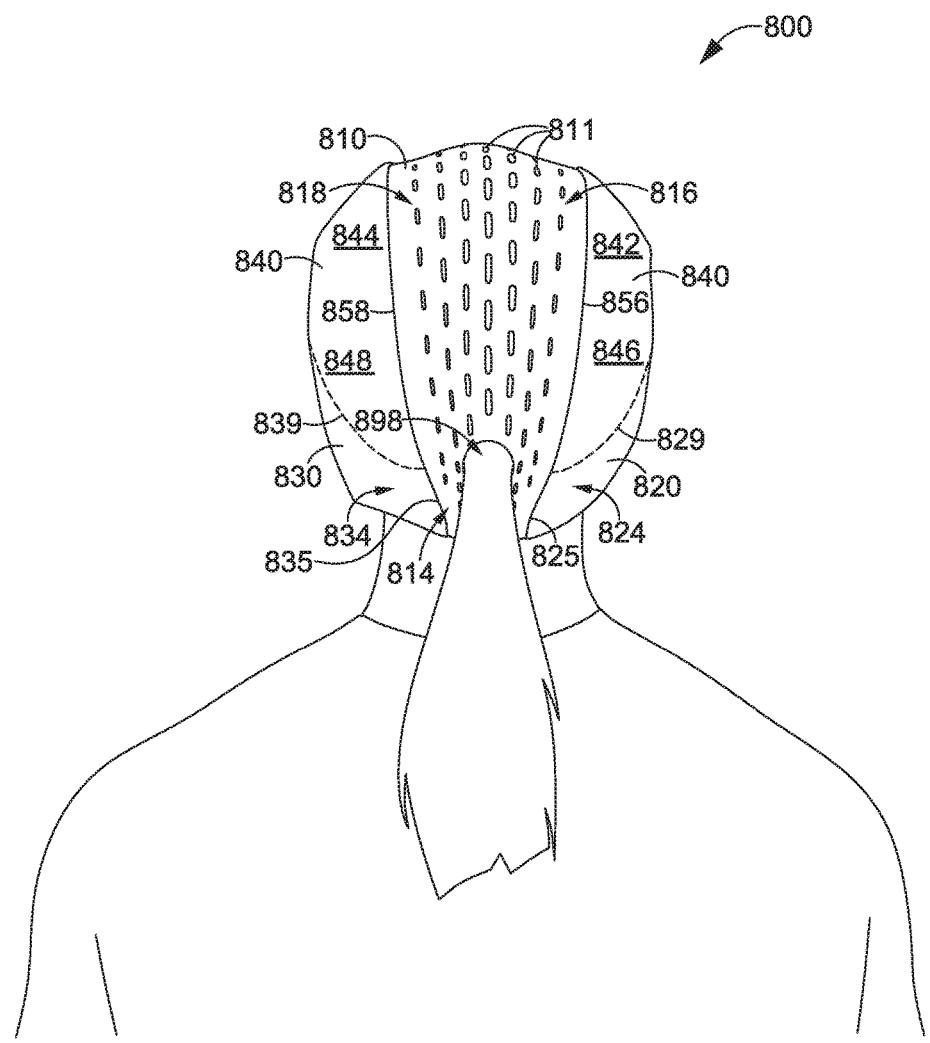
FIG. 12E depicts a rear elevation view of an alternative exemplary implementation of a cooling headgear in accordance with aspects herein.

FIG. 12E illustrates another example of the cooling headgear 800 having a ponytail opening 898. The ponytail opening 898 extends through the material layers of the vent panel 810 proximate the posterior region 814 of the vent panel 810. The ponytail opening 898 may be placed such that a gathering of hair at the back of a user's head may extend through the ponytail opening 898.

Figure 13:
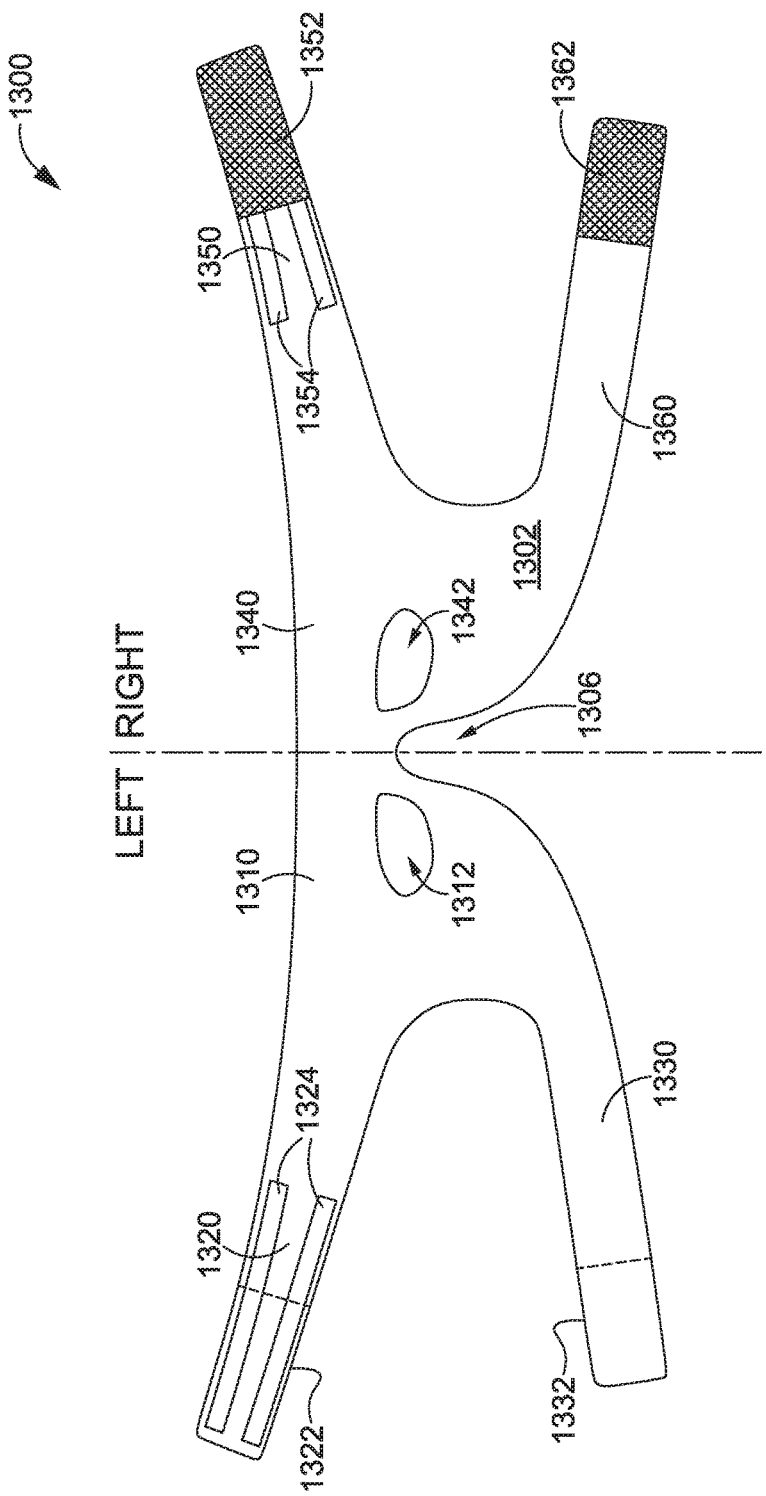
FIG. 13 depicts a front plan view of an exemplary cooling mask in a laid-flat configuration in accordance with aspects herein.

Referring now to FIG. 13, a plan view of an exemplary cooling mask 1300 is illustrated in accordance with aspects herein. The cooling mask 1300 may be worn in association with the cooling headgear 100 or 800 or, alternatively, the cooling mask 1300 may be worn by itself to provide a more limited cooling effect. The cooling mask 1300 has an inner surface 1302, which is visible in FIG. 13, and an outer surface 1304, which is not shown in FIG. 13. The cooling mask 1300 includes a left face portion 1310, a left superior strap 1320, a left inferior strap 1330, a right face portion 1340, a right superior strap 1350, and a right inferior strap 1360. The cooling mask 1300 may be comprised of the mask material 200 of FIG. 6, described above.

The left face portion 1310 includes an eye opening 1312 proximate a nose opening 1306 in the center of the mask 1300. Extending distally or laterally away from the left face portion 1310 is the left superior strap 1320. The left superior strap 1320 includes a fastener 1322 and anti-slip strips 1324. The fastener 1322 may be any of a number of reversible attachment mechanisms including, for example, hook-and-loop fasteners, buttons, snaps, buckles, clips, clasps, hook-and-eye fasteners, and the like. The anti-slip strips 1324 may be comprised of thermoplastic polyurethane (TPU), silicone, polyurethane, and the like. Further extending laterally away from the left face portion 1310 is the left inferior strap 1330. The left inferior strap includes a fastener 1332, which may be any of the reversible attachment mechanisms mentioned above.

The right face portion 1340 includes an eye opening 3142 proximate the nose opening 1306 in the center of the mask 1300. Extending distally or laterally away from the right face portion 1340 is the right superior strap 1350. The right superior strap 1350 includes a fastener 1352 and anti-slip strips 1354. Further extending laterally away from the right face portion 1340 is the right inferior strap 1360. The right inferior strap includes a fastener 1362.

When in use, the left superior strap 1320 and right superior strap 1350 of the mask 1300 are reversibly joined together at the back of the user's head with the fasteners 1322 and 1352. The anti-slip strips 1324 and 1354 may help to grip the head of the user to prevent the mask 1300 from slipping off during activity. In addition to, or alternatively, the straps 1320 and 1350 may be affixed to the material of the cooling headgear 100 or 800 via the fasteners 1322 and 1352. Similarly, the left inferior strap 1330 and the right inferior strap 1360 of the mask 1300 may be reversibly joined together at the back of the user's head with fasteners 1332 and 1362. The straps 1330 and 1360 may alternatively be affixed to the material of the cooling headgear 100 or 800 via the fasteners 1332 and 1362.

Figure 14:
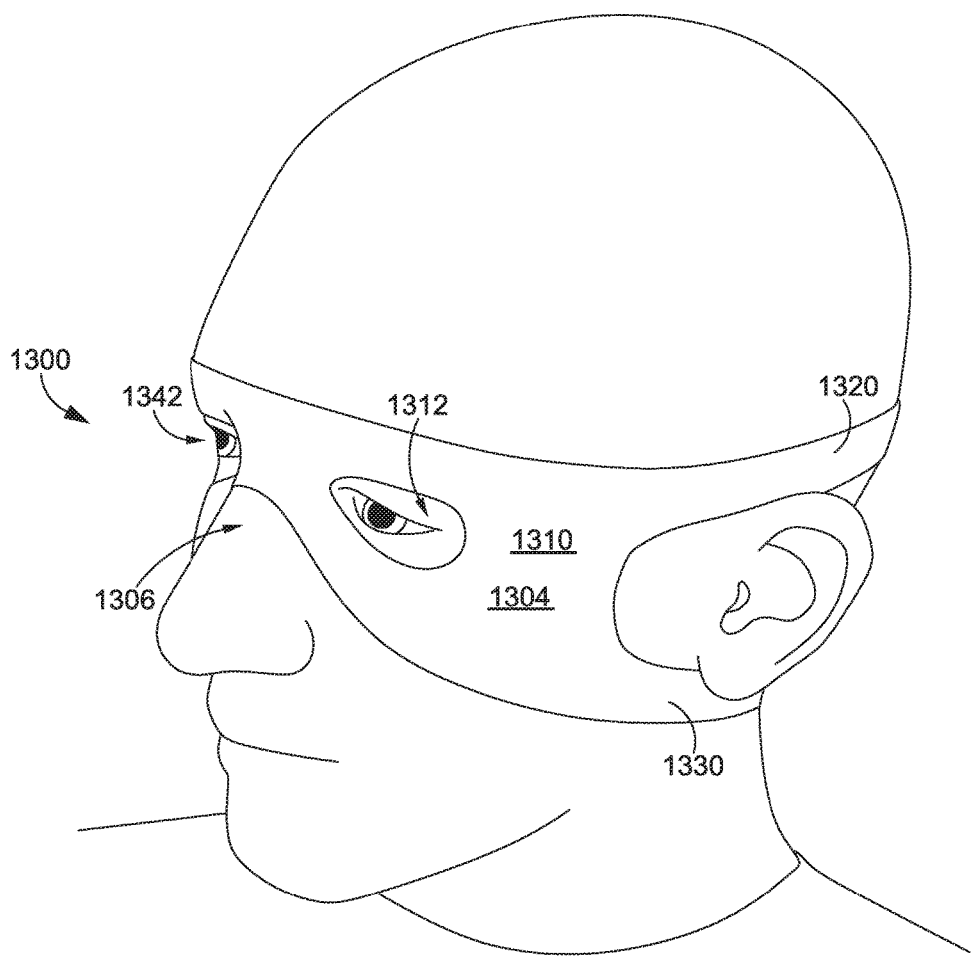
FIG. 14 depicts a perspective view of the exemplary cooling mask of FIG. 13 as worn by a user in accordance aspects herein.

FIG. 14 illustrates a perspective view of the exemplary cooling mask 1300 worn by a user in accordance with aspects herein. Although shown being worn without the cooling headgear 100 or 800, it is contemplated herein that the mask 1300 may be worn with the cooling headgear 100 or 800. The inner surface 1302 of the mask 1300 is worn against the skin of the user and is not visible. The outer surface 1304 faces away from the user and is visible. The left face portion 1310, left superior strap 1320, and left inferior strap 1330 are visible in FIG. 14. The nose opening 1306 accommodates the user's nose and centers the mask 1300 on the user's face. The left face portion 1310 covers the upper right portion of the user's face with the exception of the eye area, which is exposed by the eye opening 1312. The left superior strap 1320 extends from the left face portion 1310 over the user's ear and around the user's head. The left inferior strap 1330 extends from the left face portion 1310 under the user's ear and around the user's head.

Figure 15:
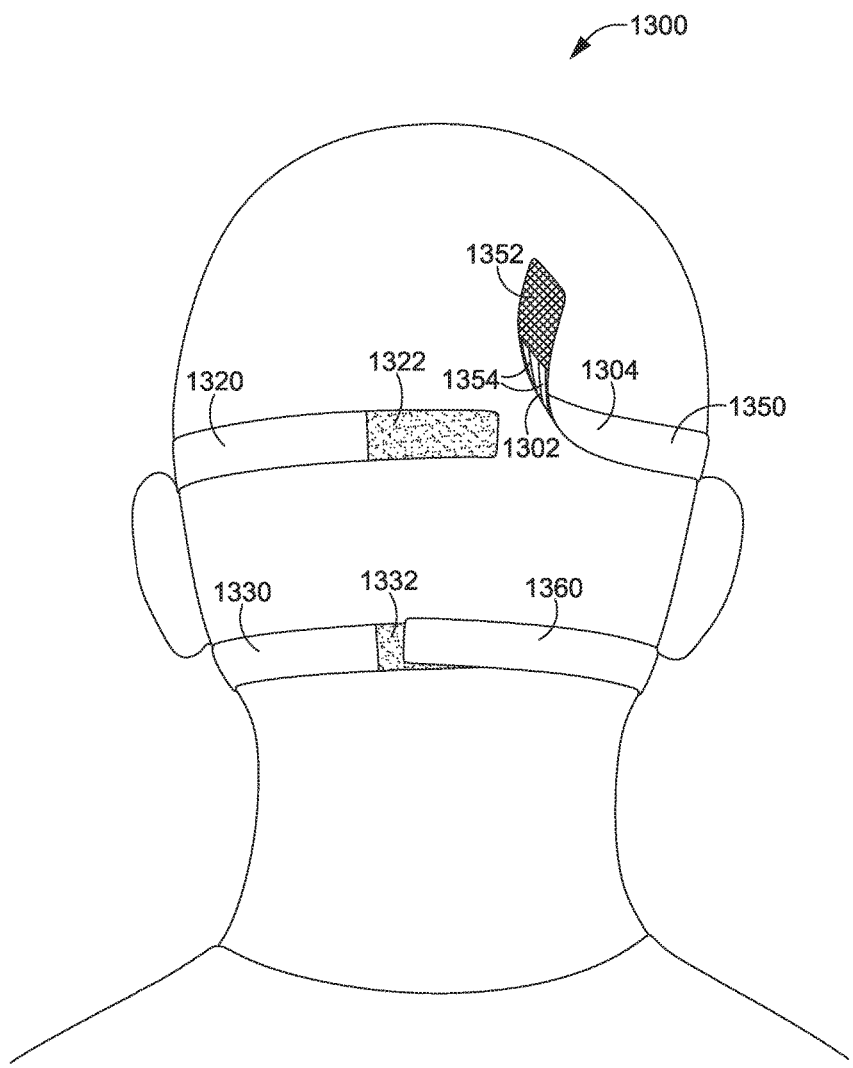
FIG. 15 depicts a rear elevation view of the exemplary cooling mask of FIG. 13 in accordance with aspects herein.

A back elevation view of the cooling mask 1300 is shown in FIG. 15 in accordance with aspects herein. The inner surface 1302 of the mask 1300 contacts the user's head and the outer surface 1304 faces away from the user when the mask 1300 is in use. The left superior strap 1320, left inferior strap 1330, right superior strap 1350, and right inferior strap 1360 are visible. The left superior strap 1320 extends horizontally around the user's head. The left superior strap 1320 includes a fastener 1322 at the distal end of the strap.

The left superior strap 1320 also includes anti-slip strips 1324 at the distal end of the strap on the inner surface 1302 of the mask 1300, which are not visible in this view. The right superior strap 1350 extends horizontally around the user's head to meet the left superior strap 1320 at the back of the user's head. The right superior strap 1350 includes a fastener 1352 at the distal end of the strap 1350. The right superior strap 1350 also includes anti-slip strips 1354 at the distal end of the strap 1350 on the inner surface 1302 of the mask 1300.

The left inferior strap 1330 also extends horizontally around the user's head, but is situated in an inferior position to the left superior strap 1320. The left inferior strap 1330 includes a fastener 1322 at the distal end. The right inferior strap 1360 extends horizontally around the user's head to meet the left inferior strap 1330 at the back of the user's head. The right inferior strap 1360 includes a fastener 1362 at the distal end (not visible). The straps 1320, 1330, 1350, 1360 serve to secure the cooling mask 1300 to the user's head by removably attaching the straps to one another at the back of the user's head with fasteners 1322, 1332, 1352 and 1362. The fasteners 1322, 1332, 1352 and 1362 may be any of the reversible attachment mechanisms mentioned above.

Figure 16A:
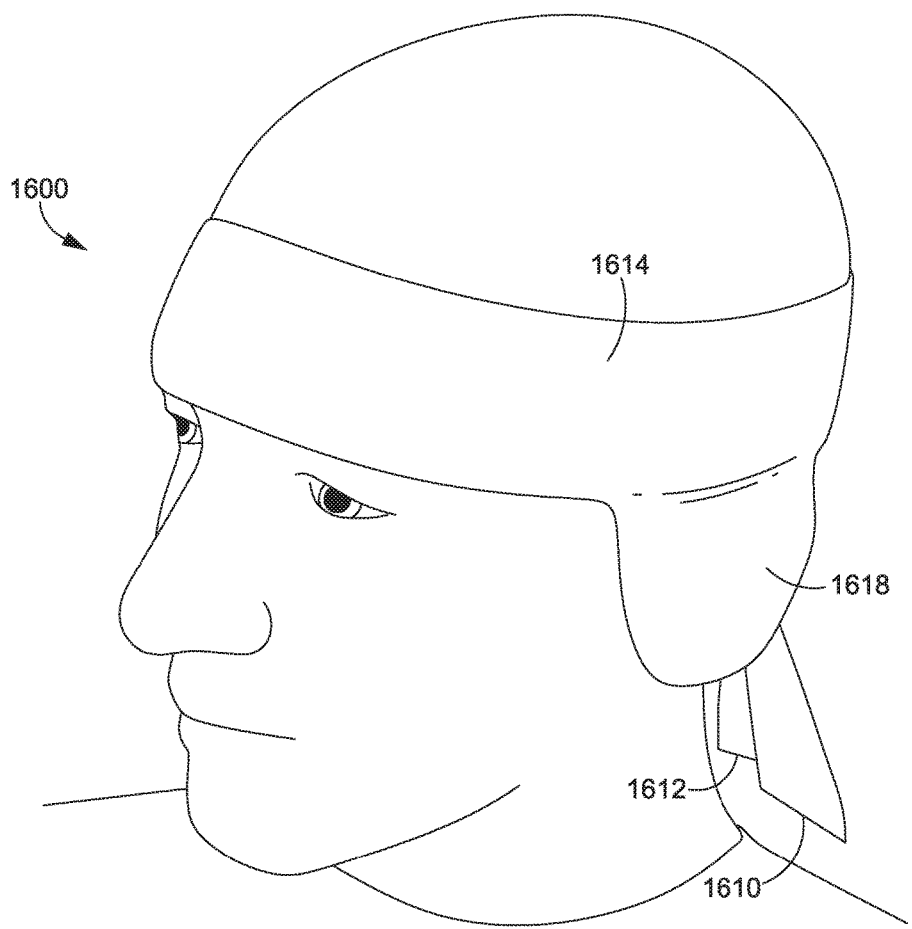
FIG. 16A depicts a front perspective view of an exemplary cooling headband as worn by a user in accordance with aspects herein.

FIG. 16A illustrates a front perspective view of an exemplary cooling headband 1600 worn by a user in accordance with aspects herein. As shown in FIG. 16B, the cooling headband 1600 is in the form of a rectangular piece of material formed from the mask material 200 as shown in FIG. 6. The cooling headband 1600 comprises a first end 1610, a second end 1612, and an intervening portion 1614 extending between the first end 1610 and the second end 1612. In an optional aspect, the headband 1600 may further comprise a first ear flap 1616 and a second ear flap 1618 that extend from an inferior margin of the headband 1600 and are adapted to cover the ears of a user when the headband 1600 is worn. In exemplary aspects, the ear flaps 1616 and 1618 may be removably affixed to the headband 1600 when needed to provide an additional cooling effect. Alternatively, the ear flaps 1616 and 1618 may be permanently affixed to the headband 1600. Any and all aspects, and any variation thereof, are contemplated as being within the scope herein.

The headband 1600 may have a length sufficient for the center of the intervening portion 1614 to be placed in contact with a user's forehead and the ends 1610 and 1612 wrapped around the user's head and secured in the back of the user's head. Securing the first and second ends 1610 and 1612 may be by tying the ends 1610 and 1612 together or releasably attaching the ends together via, for example, snaps, buttons, hook-and-loop fasteners, and the like. The cooling headband 1600 provides yet another way to the cool a user.

The cooling assemblies as described herein are used by saturating the cooling assemblies with cool water. The absorbent material soaks up the water and holds it within the cooling assembly. The cooling assembly is then placed over and/or around the head of a user. Alternatively, the cooling assembly could be placed on the head of the user and then cool water is applied to the user's head. The absorbent material within the cooling assembly absorbs the water as it is poured over the head of the user. The cooling assembly cools the head of the user as the water evaporates from the cooling assembly. The cooling assembly is particularly useful in warm weather conditions for outdoor physical activity.

The present invention has been described in relation to particular examples, which are intended in all respects to be illustrative rather than restrictive. Alternative embodiments will become apparent to those of ordinary skill in the art to which the present invention pertains without departing from its scope. Certain features and subcombinations are of utility and may be employed without reference to other features and subcombinations and are contemplated within the scope of the claims.

The invention claimed is:

1. A cooling assembly, comprising:
   one or more panels affixed together to form the cooling assembly, at least a portion of the one or more panels comprising an exterior material layer, an interior material layer, and an absorbent material layer maintained between the exterior material layer and the interior material layer, wherein:
   the cooling assembly is configured to at least partially cover a head area of a user when the cooling assembly is worn, and
   the one or more panels circumscribe a right ear opening and a left ear opening, wherein each of the right ear opening and the left ear opening extend through the exterior material layer, the interior material layer, and the absorbent material layer.

2. The cooling assembly of claim 1, wherein the cooling assembly further comprises a vent panel, extending along a longitudinal mid-line, from an anterior portion of the cooling assembly to a posterior portion of the cooling assembly, wherein the vent panel comprises a plurality of apertures.

3. The cooling assembly of claim 1, further comprising a neck panel extending from a posterior portion of the cooling assembly.

4. The cooling assembly of claim 1, wherein the absorbent material layer is comprised of superabsorbent fibers.

5. The cooling assembly of claim 4, wherein the superabsorbent fibers are comprised of a cross-linked terpolymer.

6. The cooling assembly of claim 5, wherein the cross-linked terpolymer is produced by polymerizing acrylic acid, methyl acrylate, and sodium hydroxide in water.

7. The cooling assembly of claim 1, wherein the exterior material layer and the interior material layer are bonded together at one or more location on the cooling assembly.

8. The cooling assembly of claim 7, wherein the exterior material layer is bonded to the interior material layer using an ester polyurethane adhesive film.

9. A cooling headgear, comprising:
   a plurality of panels affixed together to form the cooling headgear, at least a portion of the plurality of panels comprising an exterior material layer, an interior material layer, and an absorbent material layer maintained between the exterior material layer and the interior material layer, the plurality of panels comprising at least:
   a vent panel comprising an anterior region, a posterior region, a right side, and a left side, the vent panel further comprising a plurality of apertures that extend through the exterior material layer, the interior material layer, and the absorbent material layer;
   a superior panel comprising a right superior region, a left superior region, a right inferior region, a left inferior region, a center superior region, and a center inferior region, wherein:
   the center superior region of the superior panel is attached to the anterior region of the vent panel,
   the right superior region of the superior panel is attached to the right side of the vent panel, and
   the left superior region of the superior panel is attached to the left side of the vent panel, a right inferior panel comprising an anterior region, a posterior region, a superior region, and an inferior region, wherein:
  the posterior region of the right inferior panel is attached to the posterior region of the vent panel, and
  the superior region of the right inferior panel is attached to the right inferior region of the superior panel; and
a left inferior panel comprising an anterior region, a posterior region, a superior region, and an inferior region, wherein:
  the posterior region of the left inferior panel is attached to the posterior region of the vent panel, and
  the superior region of the left inferior panel is attached to the left inferior region of the superior panel.

10. The cooling headgear of claim 9, further comprising a neck panel comprised of the exterior material layer, the absorbent material layer, and the interior material layer, the neck panel comprising a left superior region, a right superior region, a center superior region, and an inferior region, wherein:
  the center superior region of the neck panel is attached to the posterior region of the vent panel,
  the right superior region of the neck panel is attached to the posterior region of the right inferior panel, and
  the left superior region of the neck panel is attached to the posterior region of the left inferior panel.

11. The cooling headgear of claim 10, wherein the neck panel further comprises a left flap and a right flap, wherein the left flap extends laterally from the left superior region and comprises a first fastener, the right flap extends laterally from the right superior region opposite the left flap and comprises a second fastener, and wherein the first fastener is configured to be releasably coupled to the second fastener.

12. The cooling headgear of claim 10, wherein the neck panel further comprises a left shoulder extension and a right shoulder extension.

13. The cooling headgear of claim 9, further comprising an eye opening structure having at least a superior portion, a right inferior portion, and a left inferior portion, wherein the superior portion of the eye opening structure is attached to the center inferior region of the superior panel, the right inferior portion of the eye opening structure is attached to the anterior region of the right inferior panel, the left inferior region of the eye opening structure is attached to the anterior region of the left inferior panel.

14. The cooling headgear of claim 13, wherein the eye opening structure further comprises fasteners for releasably attaching sunglasses to the cooling headgear.

15. The cooling headgear of claim 9, further comprising one or more right ear openings extending through the right inferior panel and one or more left ear openings extending through the left inferior panel.

16. The cooling headgear of claim 15, wherein the one or more right and left ear openings comprise one of a single large opening, a plurality of small apertures, or a large opening into which a porous material is positioned.

17. The cooling headgear of claim 9, further comprising a ponytail opening extending through the posterior region of the vent panel.

18. The cooling assembly of claim 1, wherein the cooling assembly comprises at least one aperture defining an eye opening.

19. The cooling assembly of claim 1, wherein the circumscribed right ear opening is at least partially covered with a right ear panel, the circumscribed left ear opening is at least partially covered with a left ear panel, and wherein each of the right ear panel and the left ear panel comprise a plurality of apertures.

* * * * *